US 9,539,103 B2

(12) United States Patent
McLaughlin et al.

(10) Patent No.: US 9,539,103 B2
(45) Date of Patent: Jan. 10, 2017

(54) EXPANDABLE INTERVERTEBRAL IMPLANT

(71) Applicant: GLOBUS MEDICAL, INC., Audubon, PA (US)

(72) Inventors: Colm McLaughlin, Glenside, PA (US); Noah Hansell, King of Prussia, PA (US); Daniel Davenport, Collegeville, PA (US); Robert W. Trout, Schwenksville, PA (US); Robert Rhoads, North Wales, PA (US); George Howard, Green Lane, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/086,179

(22) Filed: Mar. 31, 2016

(65) Prior Publication Data
US 2016/0235548 A1    Aug. 18, 2016

Related U.S. Application Data

(63) Continuation-in-part of application No. 14/852,659, filed on Sep. 14, 2015, which is a continuation-in-part
(Continued)

(51) Int. Cl.
*A61F 2/44* (2006.01)

(52) U.S. Cl.
CPC ............ *A61F 2/4425* (2013.01); *A61F 2/442* (2013.01); *A61F 2220/0008* (2013.01)

(58) Field of Classification Search
CPC ......... A61B 2/44; A61B 2/447; A61B 2/4425; A61B 2/4455
(Continued)

(56) References Cited

U.S. PATENT DOCUMENTS

| 5,397,364 A | 3/1995 | Kozak et al. |
| 5,458,641 A | 10/1995 | Jiminez |

(Continued)

FOREIGN PATENT DOCUMENTS

| FR | 2727003 A1 | 5/1996 |
| WO | 9723175 A1 | 7/1997 |

(Continued)

OTHER PUBLICATIONS

Guidance Document: Intervertebral Body Fusion Device, U.S. Dept. of Health and Human Services, Food and Drug Administration (Jun. 12, 2007).

(Continued)

*Primary Examiner* — Pedro Philogene
*Assistant Examiner* — David C Comstock

(57) ABSTRACT

An implant for therapeutically separating bones of a joint has two endplates each having an opening through the endplate, and at least one ramped surface on a side opposite a bone engaging side. A frame is slideably connected to the endplates to enable the endplates to move relative to each other at an angle with respect to the longitudinal axis of the implant, in sliding connection with the frame. An actuator screw is rotatably connected to the frame. A carriage forms an open area aligned with the openings in the endplates. The openings in the endplates pass through the carriage to form an unimpeded passage from bone to bone of the joint. The carriage has ramps which mate with the ramped surfaces of the endplates, wherein when the carriage is moved by rotation of the actuator screw, the endplates move closer or farther apart.

19 Claims, 34 Drawing Sheets

Related U.S. Application Data of application No. 13/968,865, filed on Aug. 16, 2013, now abandoned, which is a continuation-in-part of application No. 13/836,687, filed on Mar. 15, 2013, now Pat. No. 9,034,045.

(58) Field of Classification Search
USPC ............... 623/17.11, 17.15, 17.16; 606/246
See application file for complete search history.

(56) References Cited

U.S. PATENT DOCUMENTS

| | | | |
|---|---|---|---|
| 5,549,612 | A | 8/1996 | Yapp et al. |
| 5,578,034 | A * | 11/1996 | Estes ............... A61B 17/8047 |
| | | | 411/909 |
| 5,861,041 | A | 1/1999 | Tienboon |
| 5,888,223 | A | 3/1999 | Bray, Jr. |
| 6,066,175 | A | 5/2000 | Henderson et al. |
| 6,129,730 | A * | 10/2000 | Bono ............... A61B 17/8047 |
| | | | 606/271 |
| 6,156,037 | A | 12/2000 | LeHuec et al. |
| 6,200,347 | B1 | 3/2001 | Anderson et al. |
| 6,206,922 | B1 | 3/2001 | Zdeblick et al. |
| 6,231,610 | B1 | 5/2001 | Geisler |
| 6,258,089 | B1 | 7/2001 | Campbell et al. |
| 6,383,186 | B1 | 5/2002 | Michelson |
| 6,432,106 | B1 | 8/2002 | Fraser |
| 6,482,233 | B1 | 11/2002 | Aebi |
| 6,540,785 | B1 | 4/2003 | Gill et al. |
| 6,558,423 | B1 | 5/2003 | Michelson |
| 6,558,424 | B2 | 5/2003 | Thalgott |
| 6,666,889 | B1 | 12/2003 | Commarmond |
| 6,740,118 | B2 | 5/2004 | Eisermann et al. |
| 6,827,740 | B1 | 12/2004 | Michelson |
| 6,899,735 | B2 | 5/2005 | Coates et al. |
| 6,972,019 | B2 | 12/2005 | Michelson |
| 7,001,432 | B2 | 2/2006 | Keller et al. |
| 7,025,787 | B2 | 4/2006 | Bryan et al. |
| 7,137,997 | B2 | 11/2006 | Paul |
| 7,147,665 | B1 | 12/2006 | Bryan et al. |
| 7,153,325 | B2 | 12/2006 | Kim et al. |
| 7,172,627 | B2 | 2/2007 | Fiere et al. |
| 7,232,464 | B2 | 6/2007 | Mathieu et al. |
| 7,276,082 | B2 | 10/2007 | Zdeblick et al. |
| 7,309,357 | B2 | 12/2007 | Kim |
| 7,320,708 | B1 | 1/2008 | Bernstein |
| 7,618,456 | B2 | 11/2009 | Mathieu et al. |
| 7,771,475 | B2 | 8/2010 | Michelson |
| 7,846,207 | B2 | 12/2010 | Lechmann et al. |
| 7,862,616 | B2 | 1/2011 | Lechmann et al. |
| 7,875,076 | B2 | 1/2011 | Mathieu et al. |
| 8,100,976 | B2 | 1/2012 | Bray et al. |
| 8,105,382 | B2 | 1/2012 | Olmos et al. |
| 8,343,222 | B2 | 1/2013 | Cope |
| 8,506,567 | B2 * | 8/2013 | Ziemek ............... A61B 17/8042 |
| | | | 606/296 |
| 8,628,560 | B2 * | 1/2014 | Moore ............... A61B 17/15 |
| | | | 606/290 |
| 2002/0010511 | A1 | 1/2002 | Michelson |
| 2002/0016595 | A1 | 2/2002 | Michelson |
| 2003/0045939 | A1 | 3/2003 | Casutt |
| 2003/0105528 | A1 | 6/2003 | Shimp et al. |
| 2003/0125739 | A1 | 7/2003 | Bagga et al. |
| 2003/0167091 | A1 | 9/2003 | Scharf |
| 2004/0078078 | A1 | 4/2004 | Shepard |
| 2004/0143270 | A1 | 7/2004 | Zucherman et al. |
| 2004/0143332 | A1 | 7/2004 | Krueger et al. |
| 2004/0176853 | A1 | 9/2004 | Sennett et al. |
| 2005/0055098 | A1 | 3/2005 | Zdeblick et al. |
| 2005/0065607 | A1 | 3/2005 | Gross |
| 2005/0149192 | A1 | 7/2005 | Zucherman et al. |
| 2005/0149193 | A1 | 7/2005 | Zucherman et al. |
| 2005/0159819 | A1 | 7/2005 | McCormack et al. |
| 2005/0171607 | A1 | 8/2005 | Michelson |
| 2005/0177236 | A1 | 8/2005 | Mathieu et al. |
| 2005/0187625 | A1 | 8/2005 | Wolek et al. |
| 2005/0240267 | A1 | 10/2005 | Randall et al. |
| 2005/0240271 | A1 | 10/2005 | Zubok et al. |
| 2005/0256574 | A1 | 11/2005 | Paul et al. |
| 2006/0085071 | A1 | 4/2006 | Lechmann et al. |
| 2006/0129240 | A1 | 6/2006 | Lessar et al. |
| 2006/0217809 | A1 | 9/2006 | Albert et al. |
| 2007/0088441 | A1 | 4/2007 | Duggal et al. |
| 2007/0123987 | A1 | 5/2007 | Bernstein |
| 2007/0135923 | A1 | 6/2007 | Peterman et al. |
| 2007/0162130 | A1 | 7/2007 | Rashbaum et al. |
| 2007/0168032 | A1 | 7/2007 | Muhanna et al. |
| 2007/0225806 | A1 | 9/2007 | Squires et al. |
| 2007/0225812 | A1 | 9/2007 | Gill |
| 2007/0233253 | A1 | 10/2007 | Bray et al. |
| 2007/0250167 | A1 | 10/2007 | Bray et al. |
| 2007/0270961 | A1 | 11/2007 | Ferguson |
| 2008/0051890 | A1 | 2/2008 | Waugh et al. |
| 2008/0051907 | A1 | 2/2008 | Marik |
| 2008/0133013 | A1 | 6/2008 | Duggal et al. |
| 2009/0076608 | A1 | 3/2009 | Gordon et al. |
| 2009/0210062 | A1 | 8/2009 | Thalgott et al. |
| 2012/0109308 | A1 | 5/2012 | Lechmann et al. |
| 2012/0185049 | A1 | 7/2012 | Varela |
| 2012/0330426 | A1 | 12/2012 | McLaughlin et al. |
| 2013/0023994 | A1 | 1/2013 | Glerum |
| 2014/0228957 | A1 * | 8/2014 | Niemiec ............... A61F 2/447 |
| | | | 623/17.16 |
| 2014/0277504 | A1 * | 9/2014 | Forton ............... A61F 2/4611 |
| | | | 623/17.16 |

FOREIGN PATENT DOCUMENTS

| | | |
|---|---|---|
| WO | 9963914 A1 | 12/1999 |
| WO | 2005007040 A1 | 1/2005 |
| WO | 2007098288 A2 | 8/2007 |
| WO | 2008014258 A2 | 1/2008 |

OTHER PUBLICATIONS

M. Spruit et al., The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

Synthes' SynFix Technique Guide device ("SynFix Technique Guide").

* cited by examiner

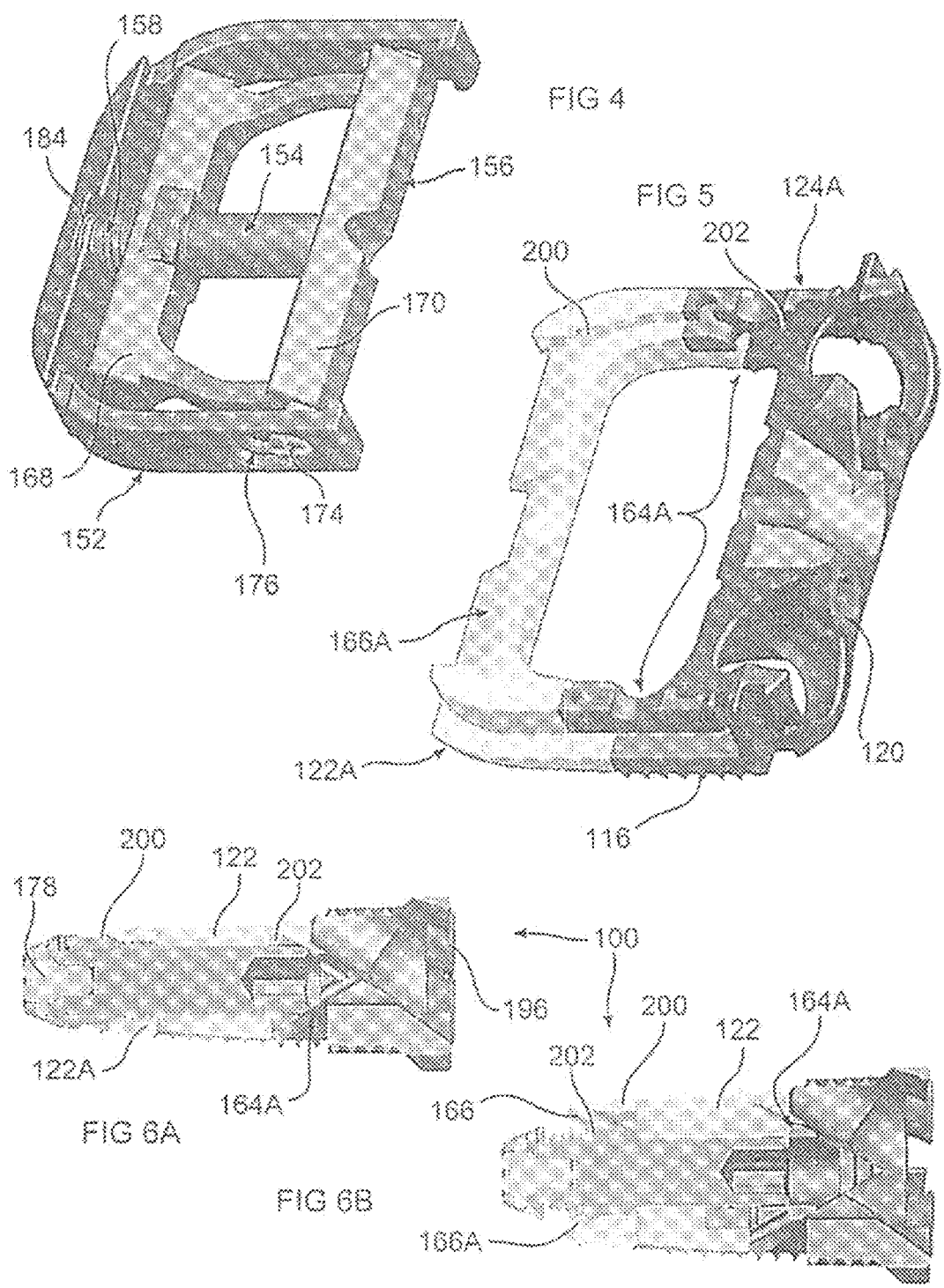

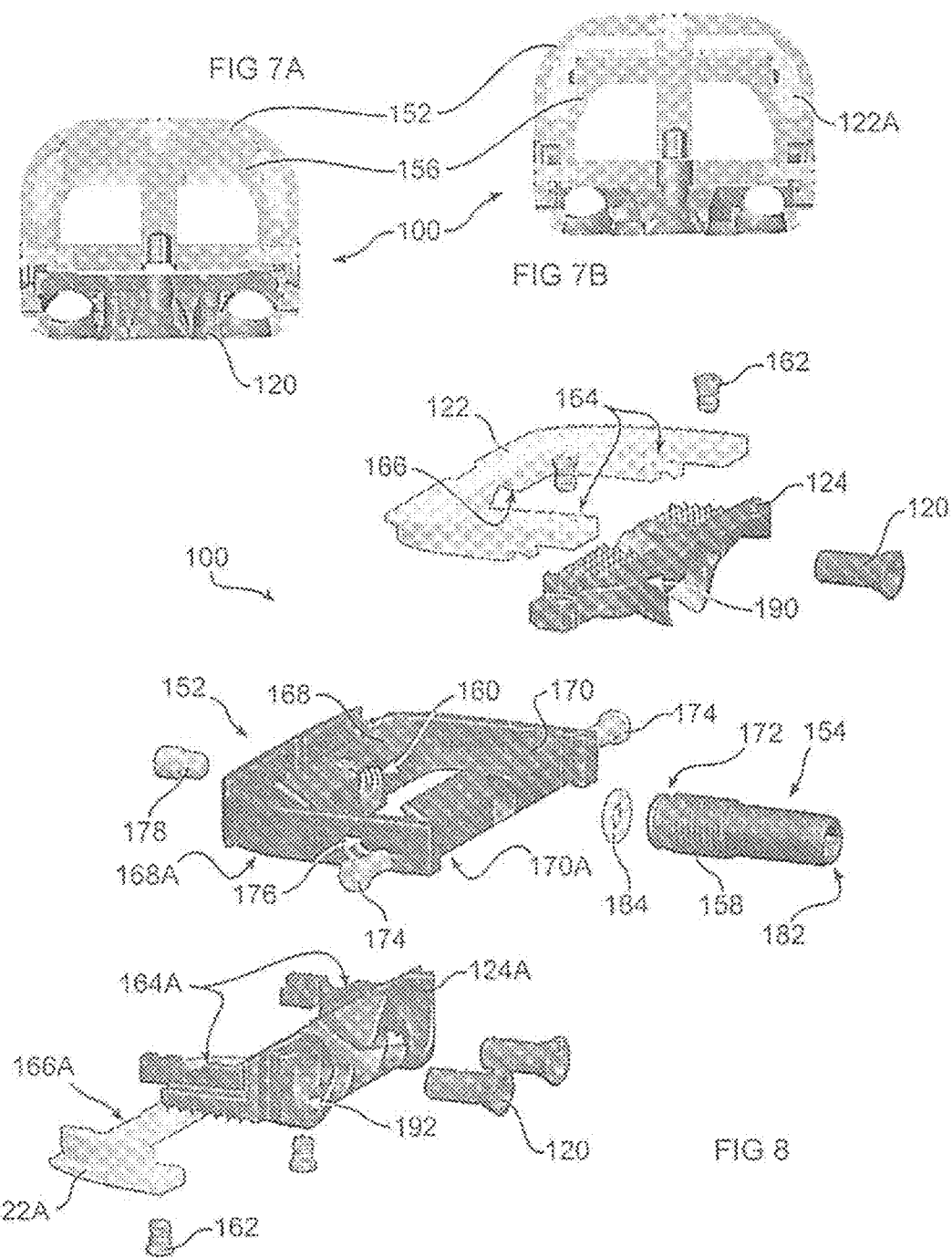

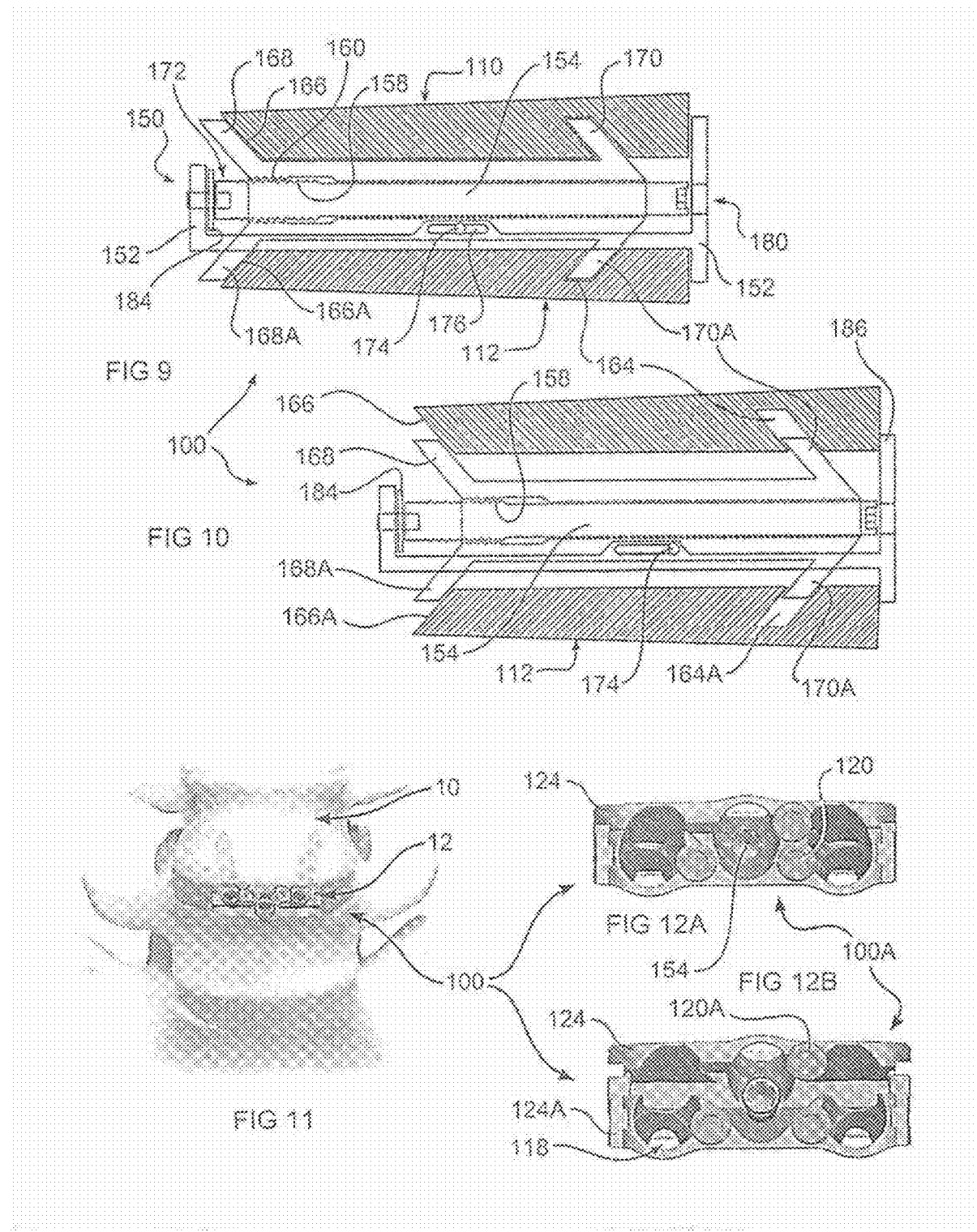

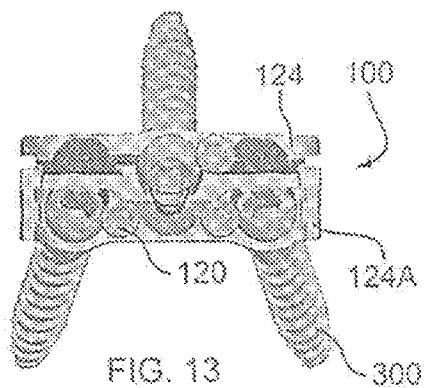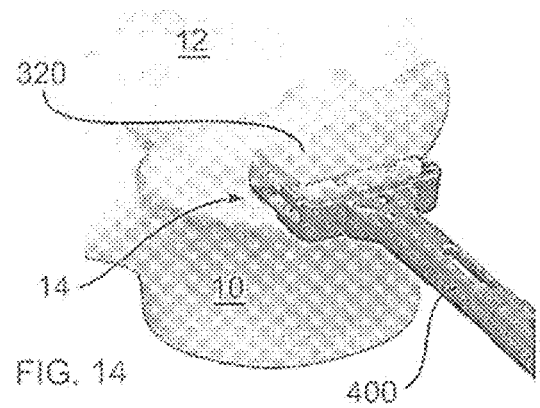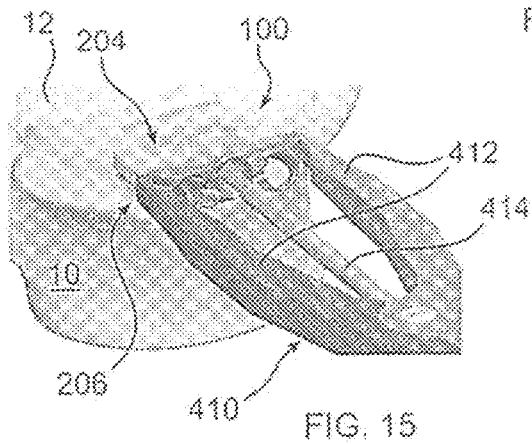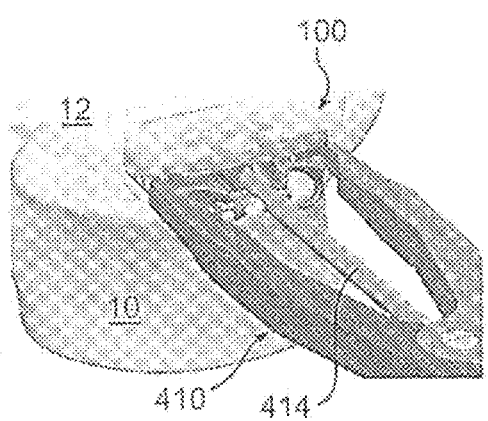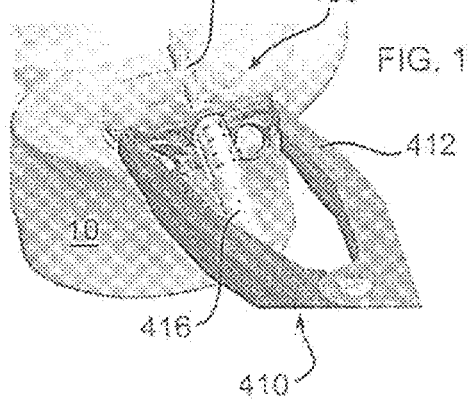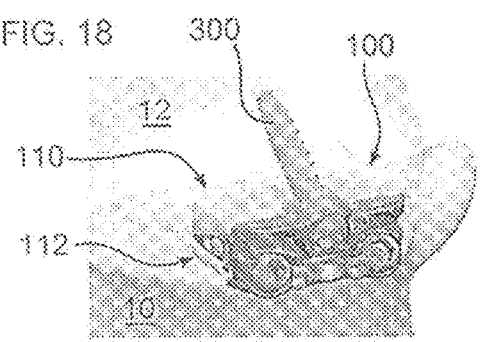

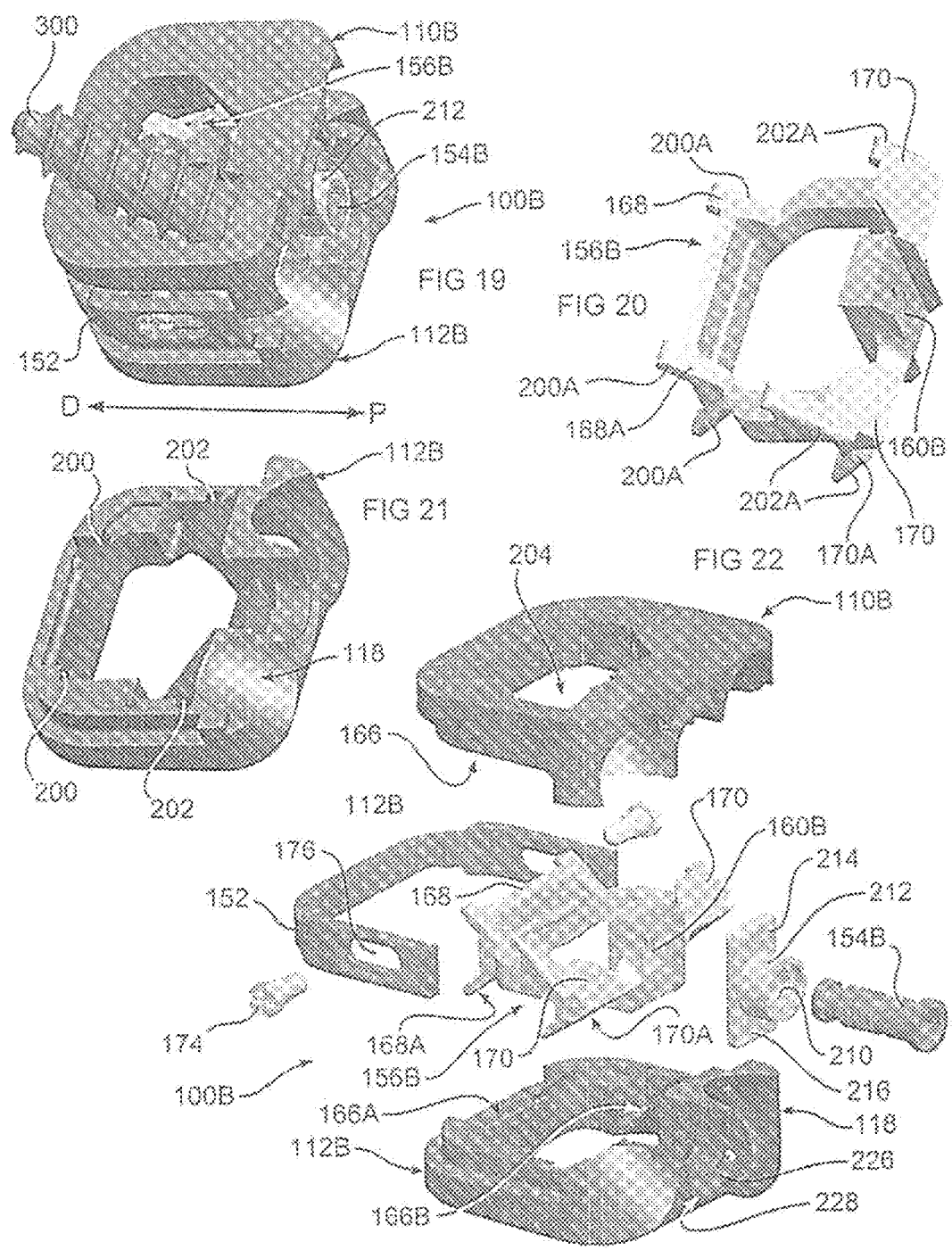

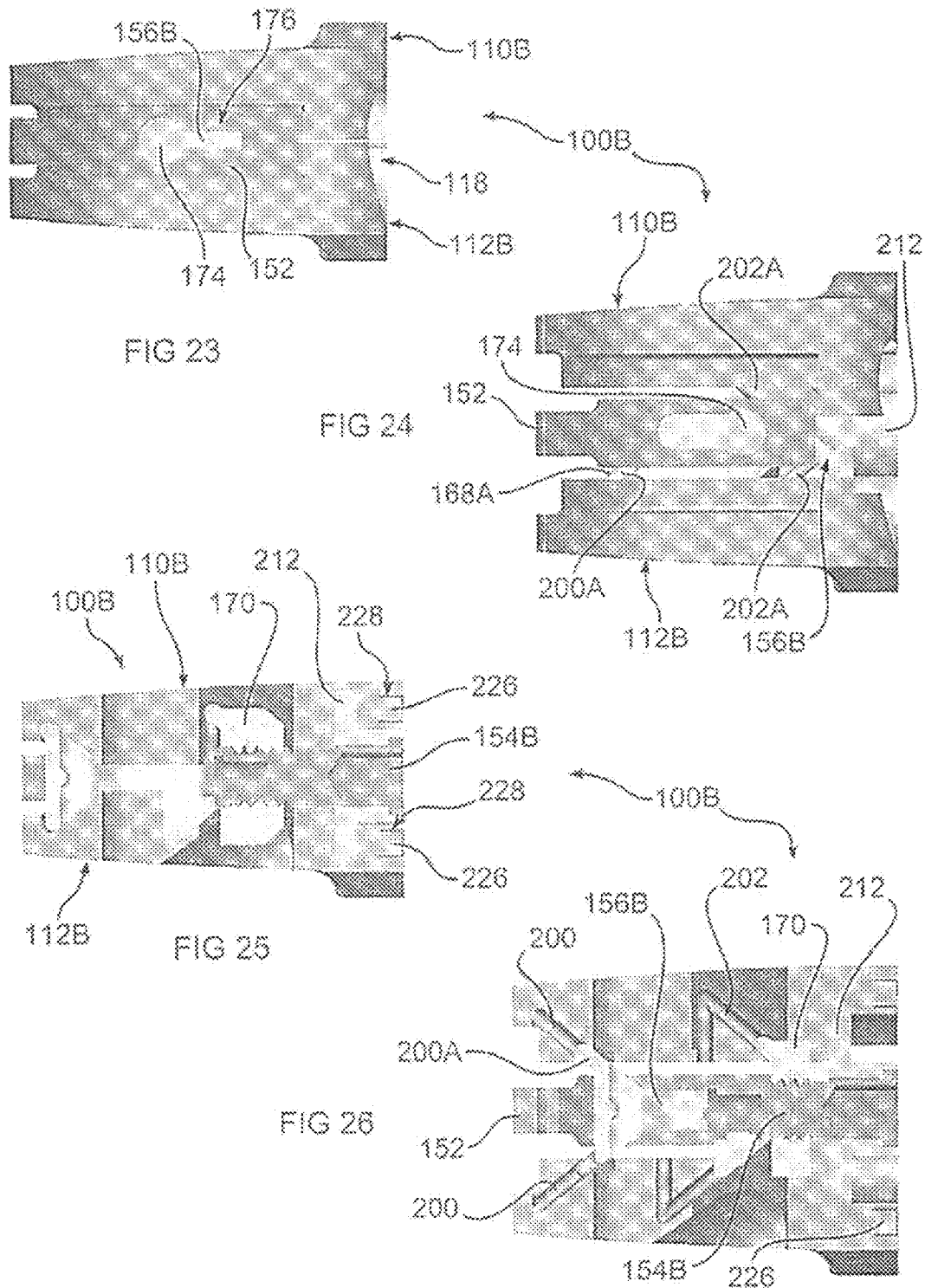

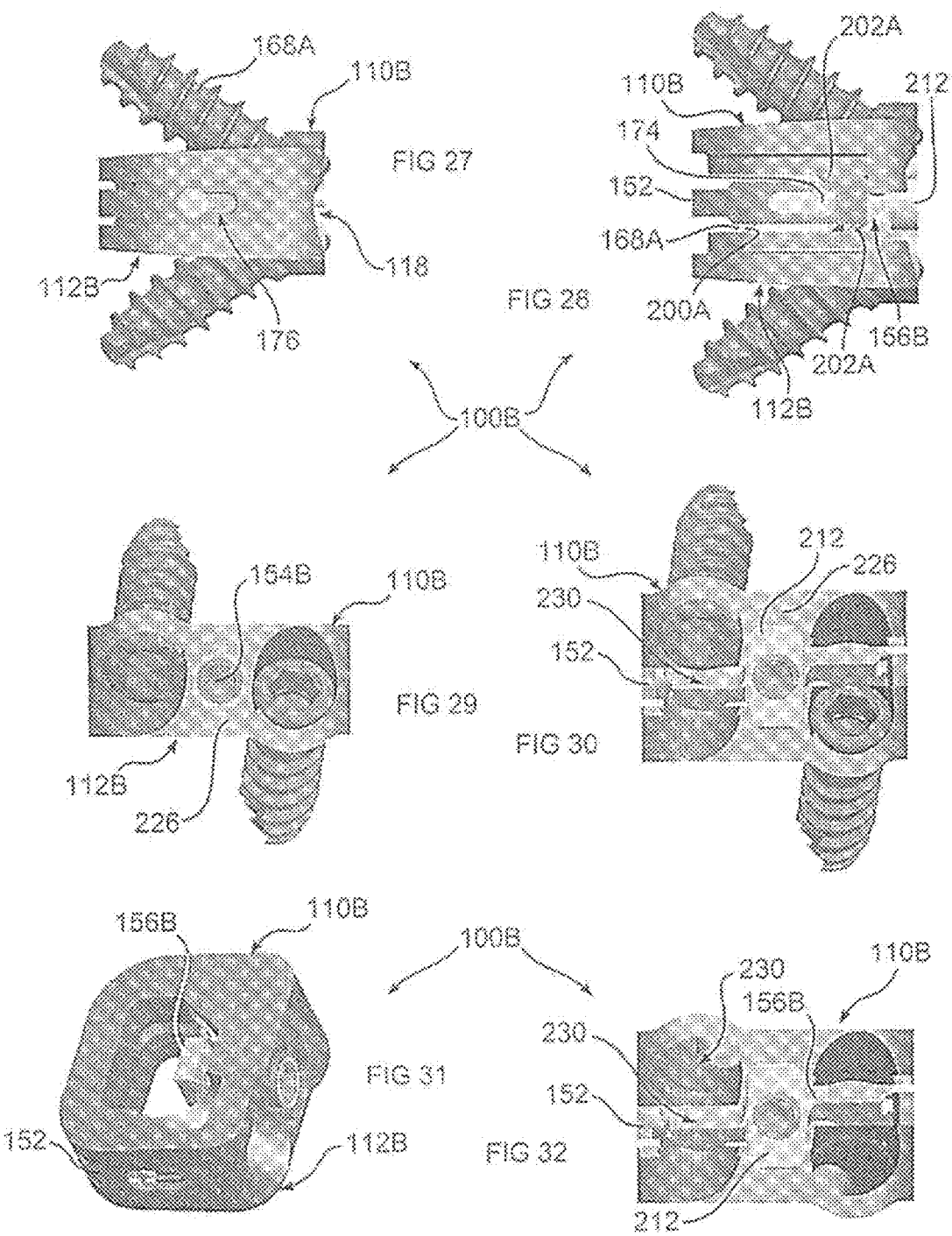

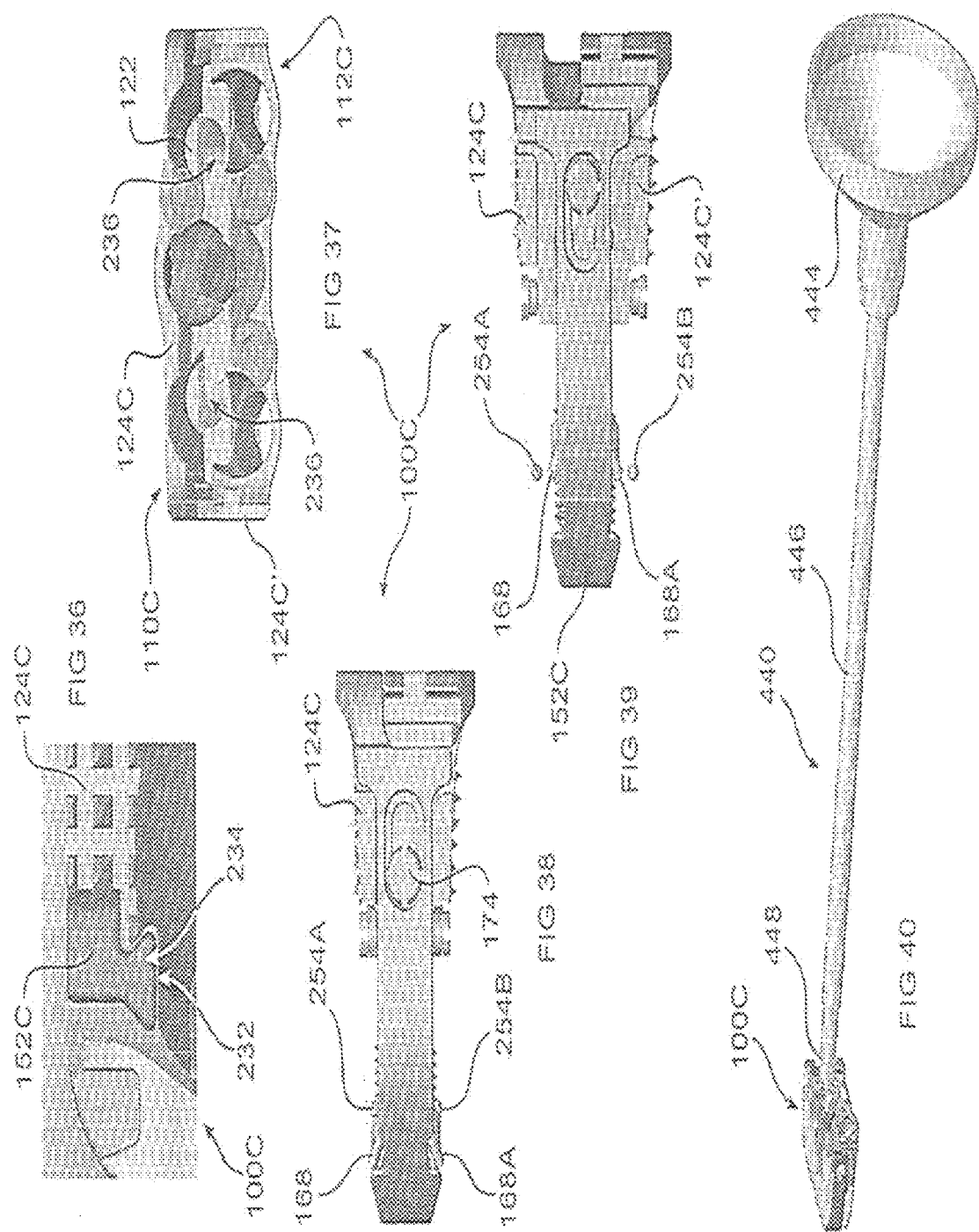

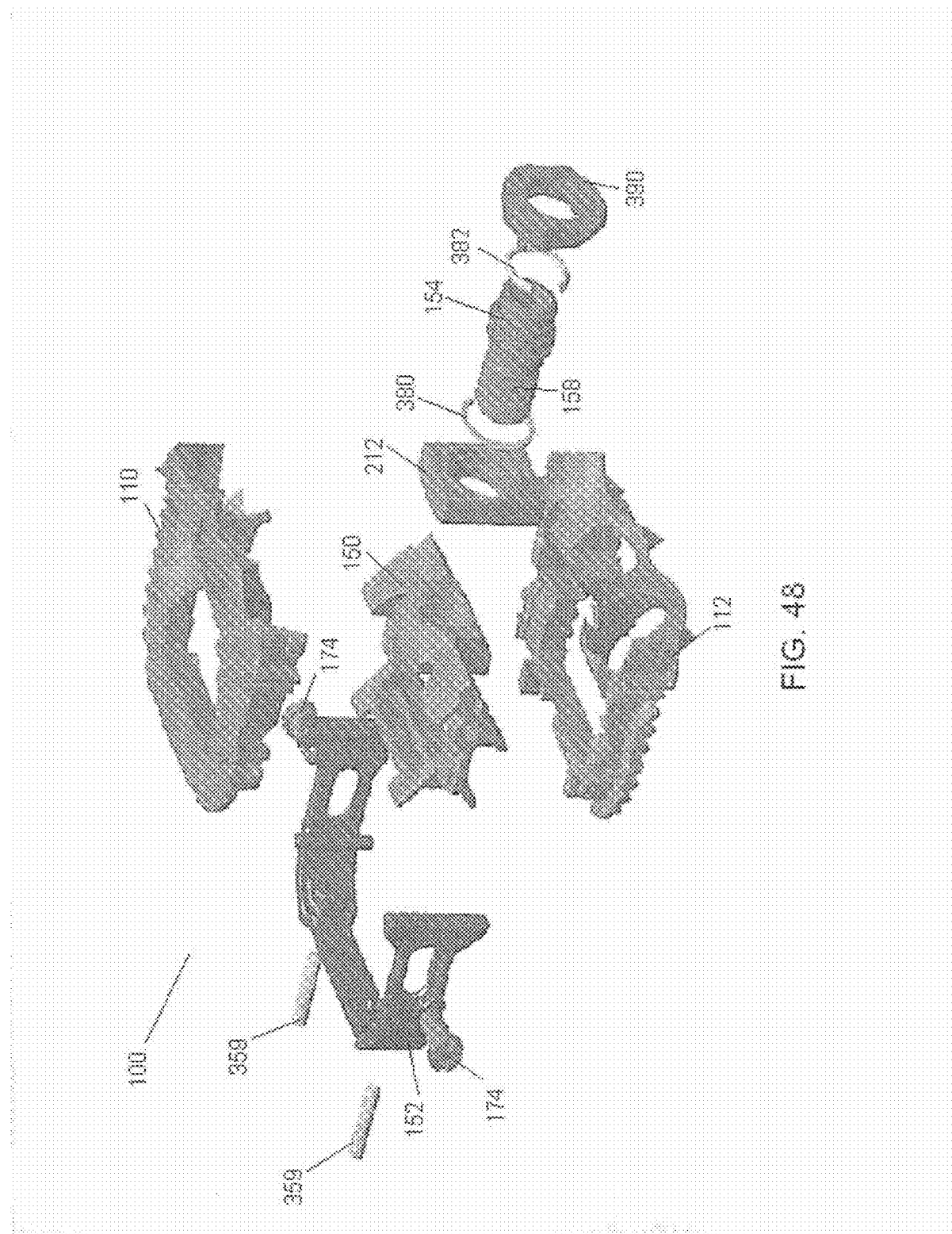

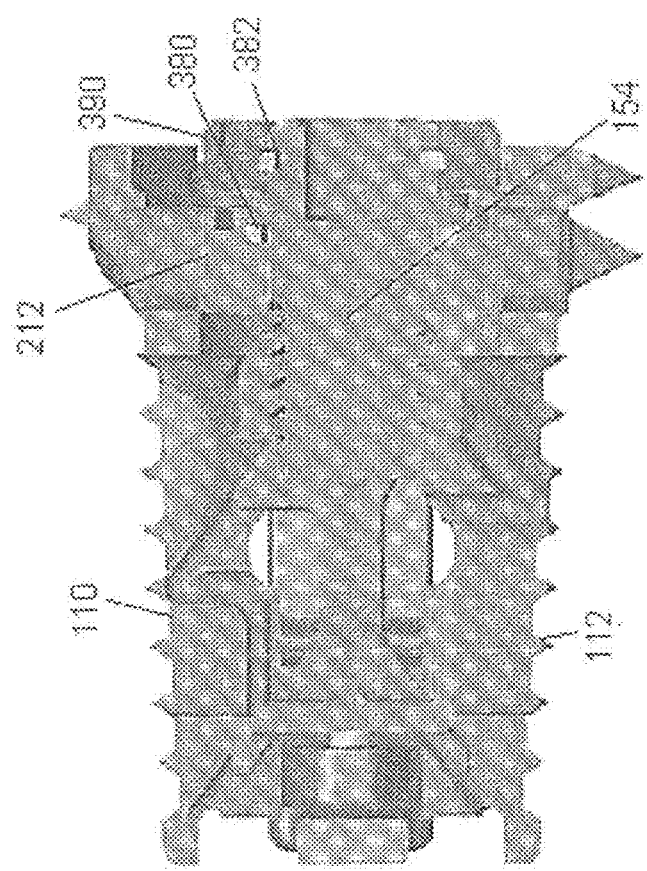
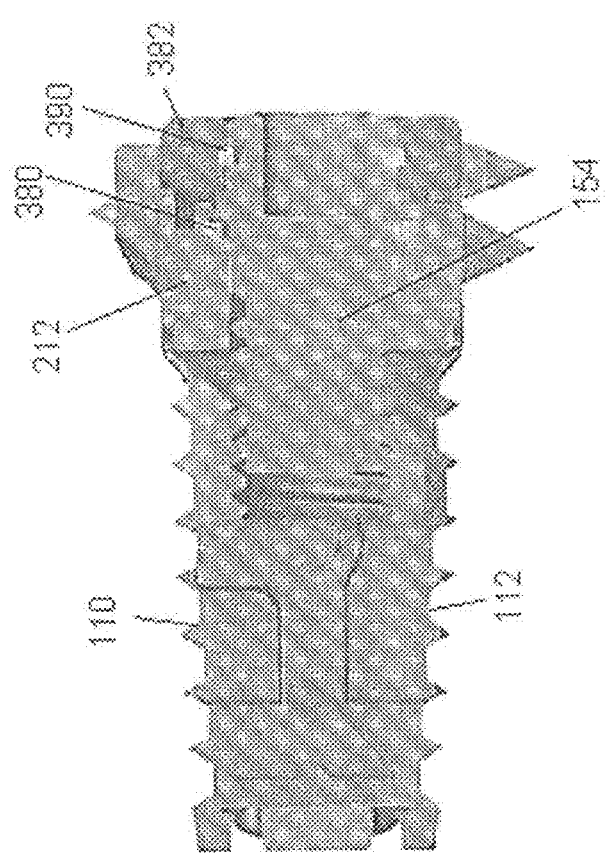
FIG. 49A
FIG. 49B

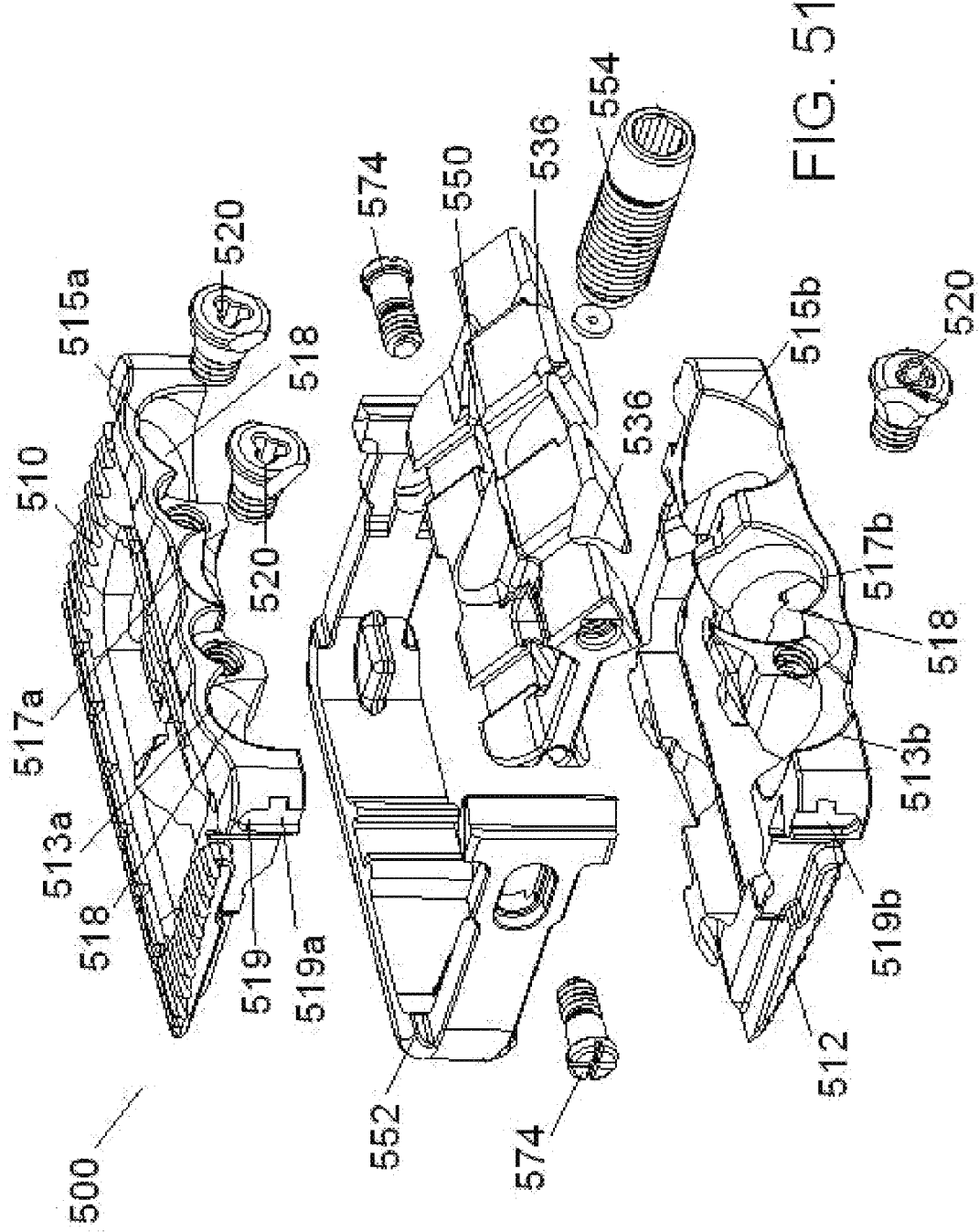

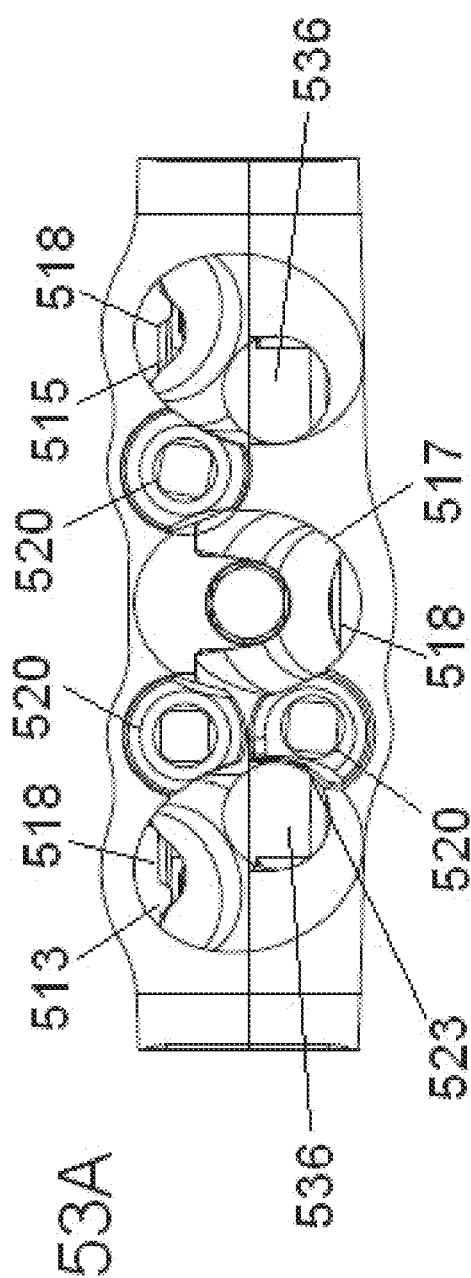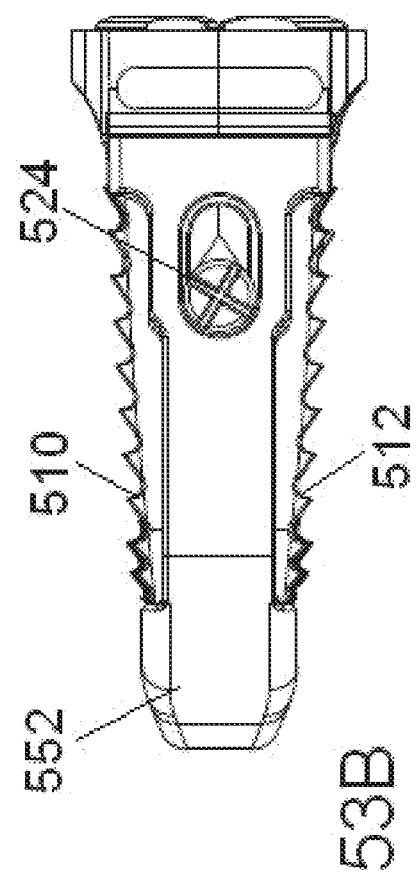
FIG. 53A
FIG. 53B

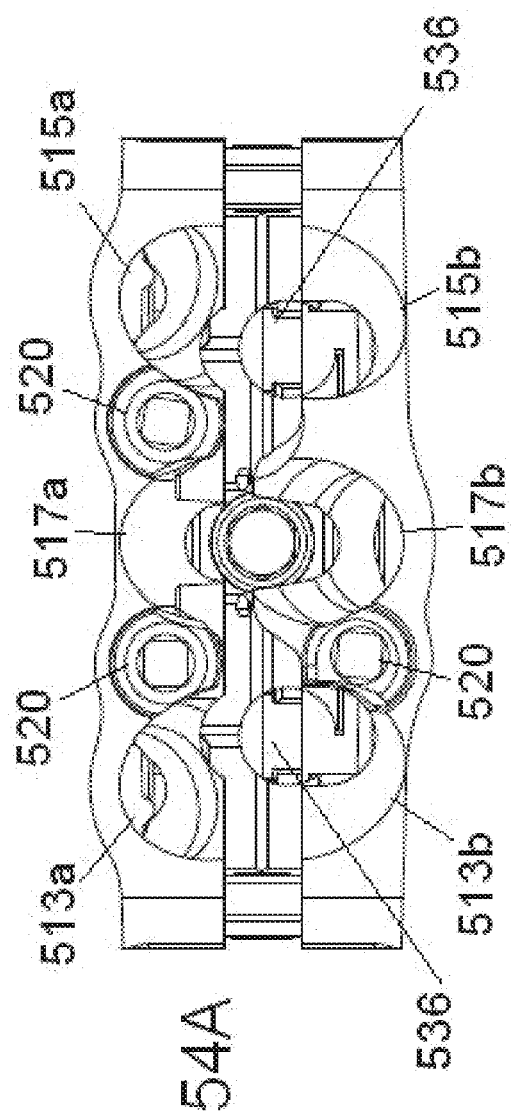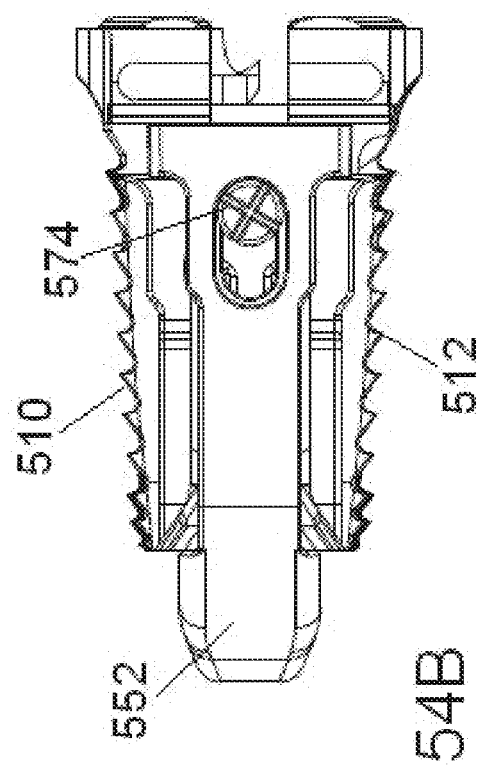
FIG. 54A
FIG. 54B

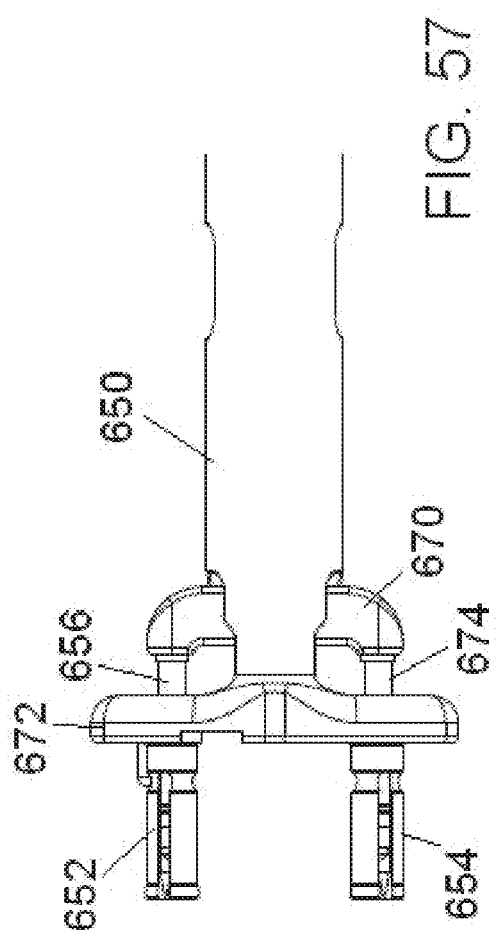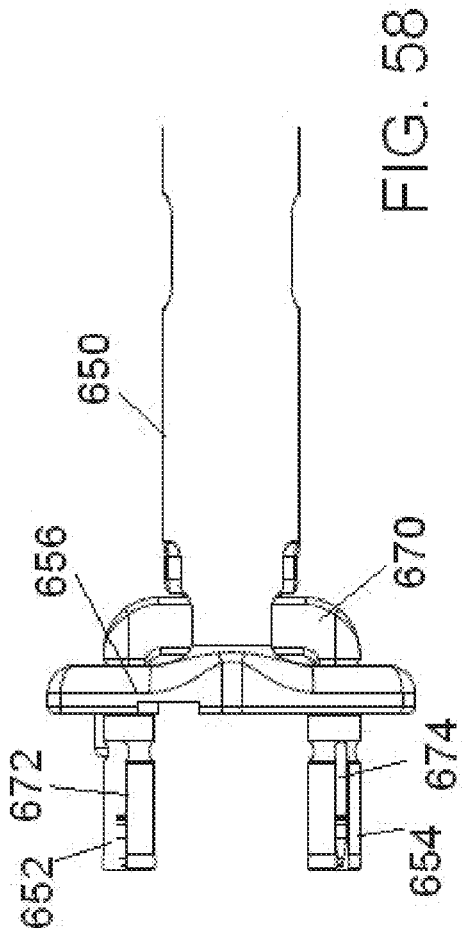

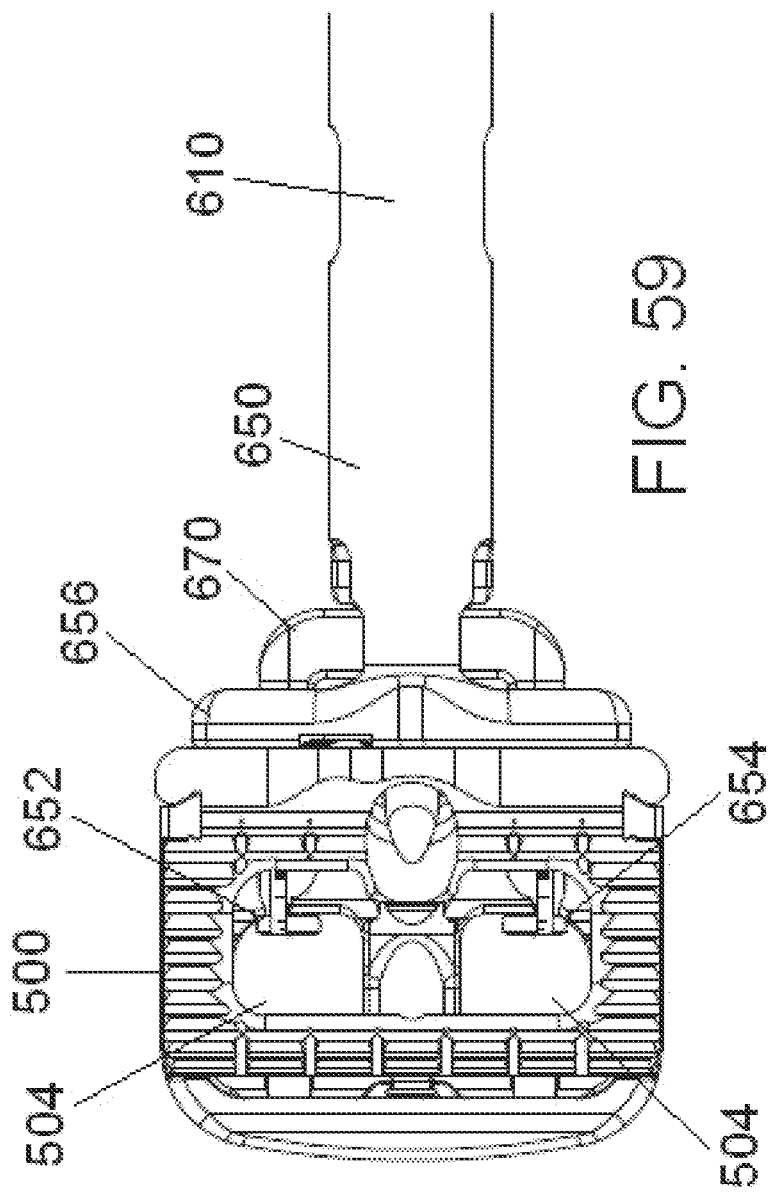

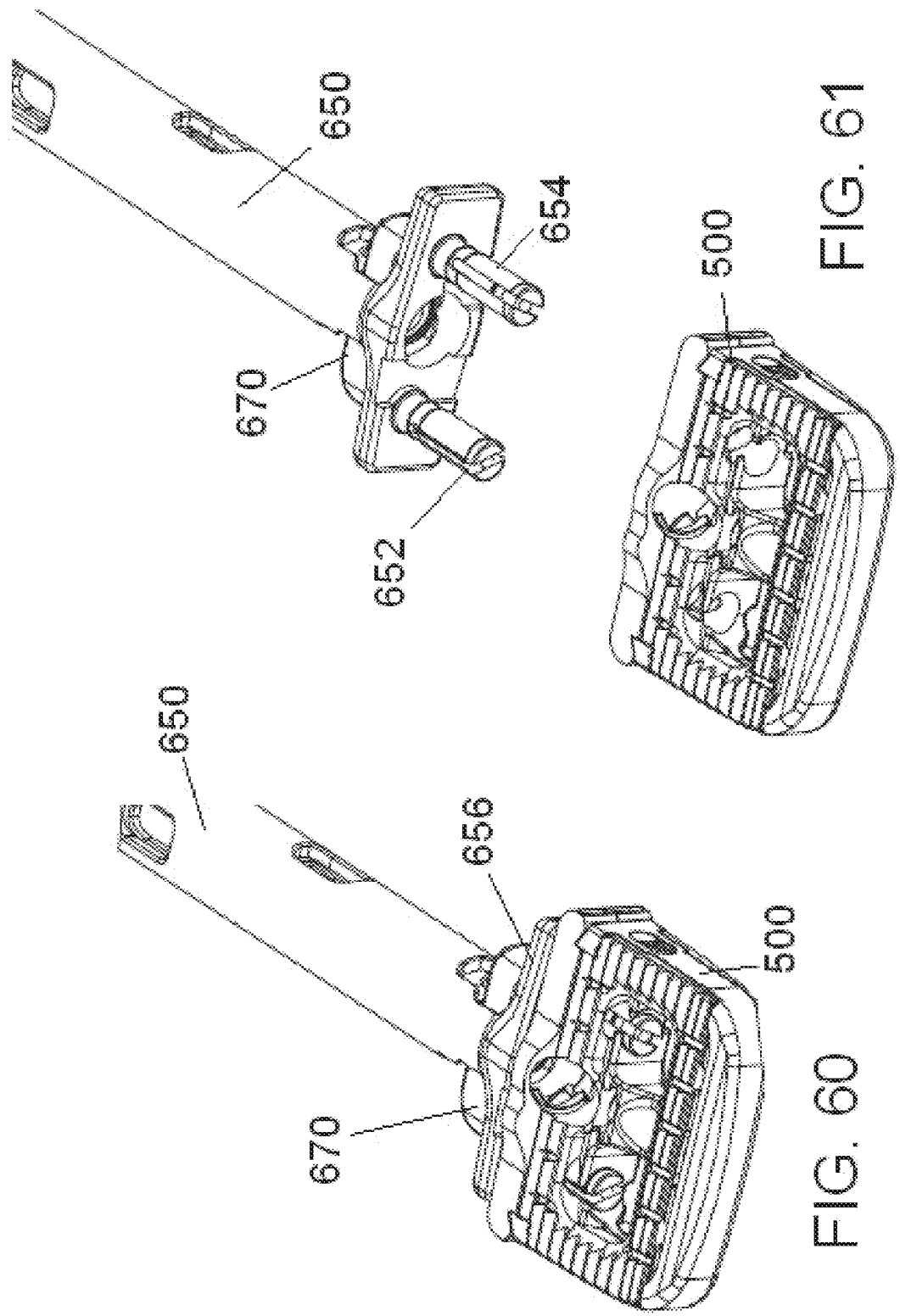

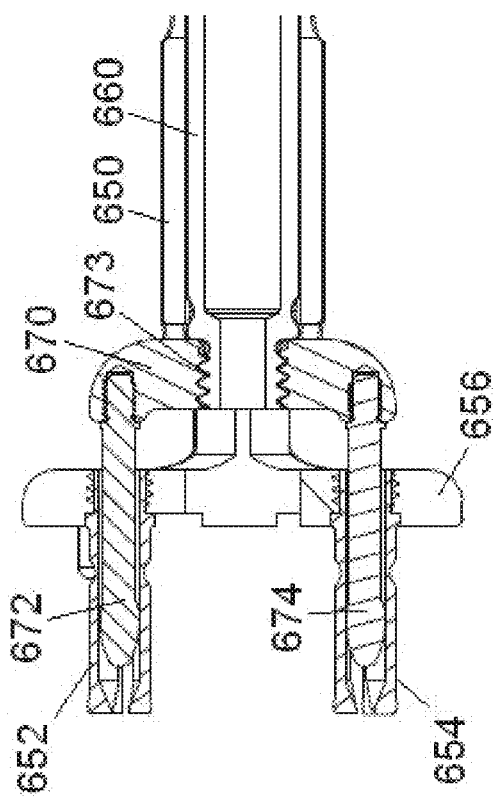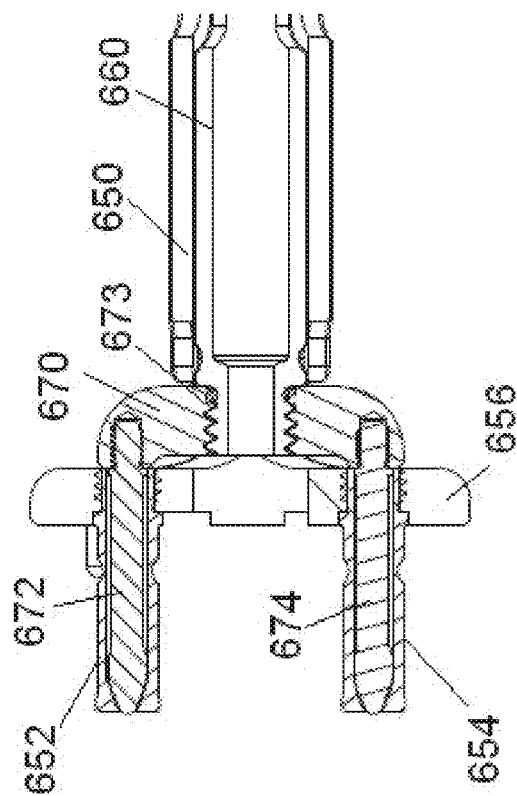

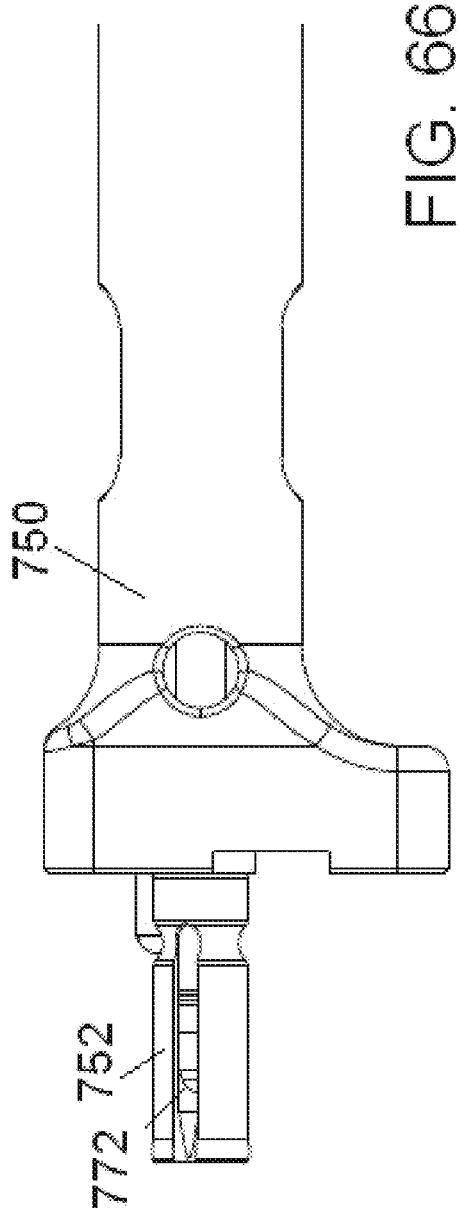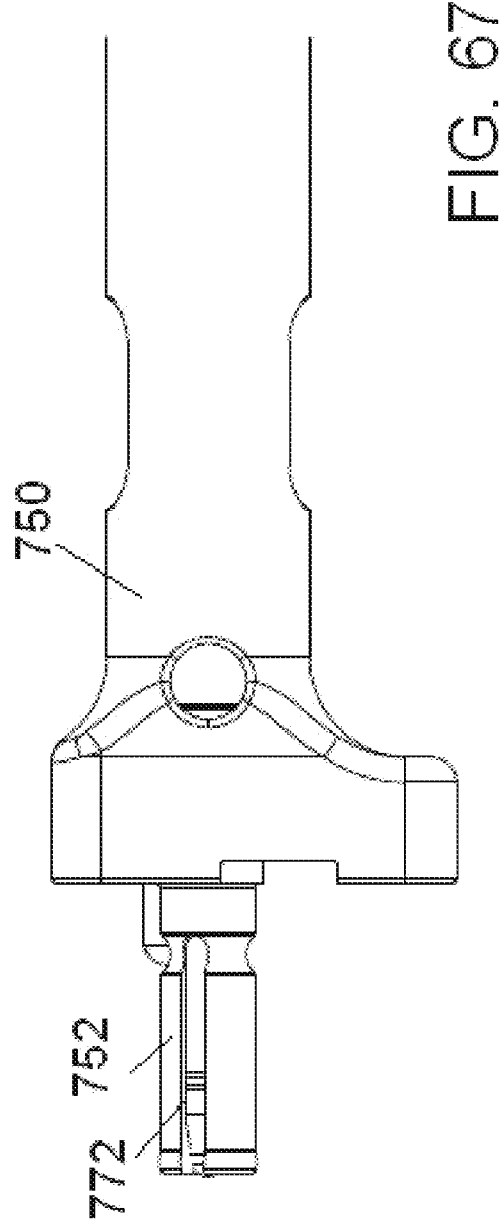

EXPANDABLE INTERVERTEBRAL IMPLANT

CROSS-REFERENCE TO RELATED APPLICATIONS

This application is a continuation-in-part of U.S. patent application Ser. No. 14/852,659, filed Sep. 14, 2015, which is a continuation-in-part of U.S. patent application Ser. No. 13/968,865, filed Aug. 16, 2013, which is a continuation in-part of U.S. patent application Ser. No. 13/836,687, filed on Mar. 15, 2013, now issued as U.S. Pat. No. 9,034,045, of which their disclosures are incorporated herein by reference in their entireties for all purposes.

FIELD OF THE INVENTION

This invention relates to stabilizing adjacent vertebrae of the spine by inserting an intervertebral implant, and more particularly an intervertebral implant that is adjustable in height.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to insert a spacer between adjacent vertebrae.

SUMMARY OF THE INVENTION

In accordance with the disclosure, an implant for therapeutically separating bones of a joint, the implant defining a longitudinal axis extending between distal and proximal ends, the implant comprises a first endplate configured to engage a first bone of the joint, and having an opening through the endplate, and at least one ramped surface on a side opposite a bone engaging side; a second endplate configured to engage a second bone of the joint, and having an opening through the endplate, and at least one ramped surface on a side opposite a bone engaging side; a frame slideably connected to the first and second endplates to enable the first and second endplates to move relative to each other at an angle with respect to the longitudinal axis, in sliding connection with the frame; an actuator screw rotatably connected to the frame; and a carriage (a) forming an open area aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; and (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame.

In various embodiments thereof, the first and second endplates are confined by the frame to move relative to each other only along an axis substantially transverse to the longitudinal axis; at least one of the first and second endplates includes at least one aperture through which a fastener may pass to secure the implant to bone of the joint; the implant further includes a blocking mechanism configured to prevent backing out of a fastener passed through at least one of the first and second endplates and into body tissue; the blocking mechanism includes a rotatable blocking member slideably retained within a channel between an unblocking position and a blocking position in which a portion of the blocking member overlaps a portion of the fastener; at least one of the first and second endplates includes one or more projections configured to engage bone of the joint when the implant is positioned between bones of the joint; at least one of the first and second endplates is composed of two interconnected portions of dissimilar materials; one of the dissimilar materials is metallic and includes at least one aperture through which a fastener may be passed to attach the implant to a bone of the joint; one dissimilar material is polymeric, and another dissimilar material is metallic; and, the implant further includes a polymeric material configured to press against the actuator screw to reduce a potential for unintended rotation of the actuator screw.

In further embodiments thereof, when the actuator screw is rotated in a first direction, a height of the implant transverse to the longitudinal axis is increased, and when the actuator screw is rotated in a second direction, a height of the implant transverse to the longitudinal axis is decreased; the actuator screw is threadably connected to the carriage along a proximal side of the carriage; the frame extends from the proximal end of the implant to the distal end of the implant, and the actuator screw is connected to the frame and threadably connected to the carriage along a distal side of the carriage; the frame is disposed within the proximal end of the implant; the frame extends from the proximal end of the implant towards the distal end of the implant; and, the implant further includes at least one post extending through the frame and into the carriage, slideably received in one of the frame or the carriage, thereby configured to maintain an alignment of the carriage along the longitudinal axis.

In yet further embodiments thereof, the implant further includes a first passage formed in a proximal end of at least one of the first and second endplates, and a second passage formed in a proximal side of the carriage, the first and second passages aligned to admit introduction of a therapeutic matter into the open area of the carriage when the implant is implanted between bones of the joint; the frame connects to the first and second endplates with a dovetail connection; the implant further includes at least one radiopaque marker positioned in connection with at least one of the first and second endplates, whereby an extent of movement of the connected endplate can be determined using imaging by a relative alignment of the radiopaque marker and a radiopaque element of the implant which does not move together with the connected endplate; ends of the at least one of the plurality of ramps of the carriage slide within grooves in at least one of the first and second endplates.

In another embodiment thereof, the frame includes an actuator screw bearing, a first tab extending away from the bearing in a first direction, and a second tab extending away from the bearing in a direction opposite to the upper tab, the first and second tabs forming edges; and the first and second endplates including grooves sized and dimensioned to slidingly receive the edges of the first and second tabs, respectively. In accordance with another embodiment of the disclosure, an implant for therapeutically separating bones of a joint, the implant defining a longitudinal axis extending between distal and proximal ends, the implant comprises a first endplate configured to engage a first bone of the joint, and having an opening through the endplate transverse to the longitudinal axis, and at least one ramped surface on a side opposite a bone engaging side; a second endplate configured to engage a second bone of the joint, and having an opening through the endplate transverse to the longitudinal axis, and at least one ramped surface on a side opposite a bone engaging side; a frame slideably connected to the first and second endplates to enable the first and second endplates to move relative to each other at an angle substantially transverse to the longitudinal axis, in sliding connection with the frame; an actuator screw rotatably connected to the frame; and a carriage (a) forming one or more open areas aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame; and (d) at least one passage formed in a proximal side of the carriage in communication with at least one proximal passage in at least one of the first or second endplates, the communicating passages configured to admit introduction of a therapeutic matter into the open area of the carriage when the implant is implanted between bones of the joint.

In accordance with the disclosure, a method of therapeutically separating bones of a joint, comprises inserting an implant defining a longitudinal axis extending between distal and proximal ends between bones of the joint, the implant including—a first endplate configured to engage a first bone of the joint, and having an opening through the endplate, and at least one ramped surface on a side opposite a bone engaging side; a second endplate configured to engage a second bone of the joint, and having an opening through the endplate, and at least one ramped surface on a side opposite a bone engaging side; a frame slideably connected to the first and second endplates to enable the first and second endplates to move relative to each other at an angle with respect to the longitudinal axis, in sliding connection with the frame; an actuator screw rotatably connected to the frame; and a carriage (a) forming one or more open areas aligned with the openings in the first and second endplates and defining thereby a proximal carriage side and a distal carriage side with respect to the longitudinal axis, (b) threadably connected to the actuator screw, whereby rotation of the actuator screw moves the carriage with respect to the frame and the first and second endplates, the actuator screw not crossing between the proximal carriage side and the distal carriage side; and (c) including a plurality of ramps each mateable with at least one of the at least one ramped surfaces of the first and second endplates, wherein when the carriage is moved by rotation of the actuator screw, at least one of the at least one ramped surface of the first endplate and at least one of the at least one ramped surface of the second endplate each slide along at least one of the plurality of ramps of the carriage to cause the endplates to move relative to each other in sliding connection with the frame; and rotating the actuator screw after the implant is inserted to move the first and second endplates relatively farther apart to separate bones of the joint.

In yet further embodiments thereof, the implant further includes a friction sleeve coupled to the actuator screw. The actuator screw together with the friction sleeve fit inside an opening in the actuator. The friction sleeve may be dimensioned to interfere with the outer diameter of the actuator screw and the inner diameter of the opening in the actuator. With this interference, friction is created between the actuator screw and the actuator in order to prevent unwanted rotation of the actuator screw. In addition, the interference and friction improves the consistency of the feel of the actuator screw when rotated by the user to expand or contract the implant.

BRIEF DESCRIPTION OF THE DRAWINGS

A more complete understanding of the present invention, and the attendant advantages and features thereof, will be more readily understood by reference to the following detailed description when considered in conjunction with the accompanying drawings, in which:

FIG. 4 depicts a carriage and frame of the implant of FIG. 1;

FIG. 5 depicts an endplate of the implant of FIG. 1;

FIG. 6A depicts a sagittal cross-section of the implant of FIG. 2;

FIG. 6B depicts a sagittal cross-section of the implant of FIG. 3;

FIG. 7A depicts an transverse cross-section of the implant of FIG. 2;

FIG. 7B depicts an transverse cross-section of the implant of FIG. 3;

FIG. 8 depicts an exploded view of the implant of FIG. 1;

FIG. 9 depicts a diagrammatic view of aspects of an implant in accordance with the disclosure, in a reduced height configuration;

FIG. 10 depicts a the implant of FIG. 9, in an expanded height configuration;

FIG. 11 depicts the implant of FIG. 1, implanted between adjacent vertebrae;

FIG. 12A depicts a front view of the implant of FIG. 1 having an alternative blocking configuration, in a reduced height configuration;

FIG. 12B depicts the implant of FIG. 12A in an expanded height configuration;

FIG. 13 depicts the implant of FIG. 12B, with bones screws inserted into the implant;

FIG. 14 depicts inserting a trial of the disclosure, the trial representing an implant of the disclosure, into the disc space, using a trialing tool of the disclosure;

FIG. 15 depicts an implantation and actuating tool of the disclosure inserting an implant of the disclosure into the disc space;

FIG. 16 depicts the implant and tool of FIG. 14, the tool having expanded the implant;

FIG. 17 depicts the implant and tool of FIG. 15, and a bone screw driver inserting a bone screw;

FIG. 18 depicts the implant of FIG. 13 secured between vertebrae;

FIG. 19 depicts an implant of the disclosure including a proximally driven carriage;

FIG. 20 depicts the carriage of the implant of FIG. 19;

FIG. 21 depicts a lower endplate of the implant of FIG. 19;

FIG. 22 depicts an exploded view of the implant of FIG. 19;

FIG. 23 depicts a reduced height configuration of the implant of FIG. 19;

FIG. 24 depicts an expanded height configuration of the implant of FIG. 23;

FIG. 25 depicts a cross section of the implant of FIG. 23;

FIG. 26 depicts a cross section of the implant of FIG. 24;

FIG. 27 depicts the implant of FIG. 23, with bone screws inserted into the implant;

FIG. 28 depicts the implant of FIG. 24, with bone screws inserted into the implant;

FIG. 29 depicts a front view of the implant of FIG. 27;

FIG. 30 depicts a front view of the implant of FIG. 28;

FIG. 31 depicts a perspective view of the implant of FIG. 19, without bone screws inserted;

FIG. 32 depicts a front view of the implant of FIG. 30, without bone screws inserted;

FIG. 36 depicts an enlarged cross section of a dovetail connection of the implant of FIG. 33;

FIG. 37 depicts a front view of the implant of FIG. 33, illustrating passages for bone graft material;

FIG. 38 depicts a simulating of radiographic imaging of an implant of the disclosure, illustrating radiographic markers, the implant in a reduced height configuration;

FIG. 39 depicts the implant of FIG. 38, the implant in an expanded height configuration;

FIG. 40 depicts a bone funnel of the disclosure, used in connection with an implant of the disclosure;

FIG. 48 depicts an exploded view of an alternative expandable implant including endplates formed primarily of metal in accordance with embodiments of the present application;

FIGS. 49A and 49B depict unexpanded and expanded configurations of the expandable implant in FIG. 48.

FIG. 51 is an exploded view of an alternative implant in accordance with some embodiments.

FIGS. 53A and 53B are different views of the implant of FIG. 51 in an unexpanded configuration.

FIGS. 54A and 54B are different views of the implant of FIG. 51 in an expanded configuration.

FIG. 57 is a close-up view of the insertion tool of FIG. 55 with an implant in a retracted position.

FIG. 58 is a close-up view of the insertion tool of FIG. 55 with an implant in an engaged position.

FIG. 59 is top view of the insertion tool of FIG. 55 with an implant in an engaged position.

FIG. 60 is a top perspective view of the insertion tool of FIG. 55 attached to an implant.

FIG. 61 is a top perspective view of the insertion tool of FIG. 55 detached from an implant.

FIG. 62 is a close-up cross-sectional view of the insertion tool of FIG. 55 with an implant in a retracted position.

FIG. 63 is a close-up cross-sectional view of the insertion tool of FIG. 55 with an implant in an engaged position.

FIG. 65 is a close-up view of the insertion tool of FIG. 64 in a retracted position.

FIG. 66 is a close-up view of the insertion tool of FIG. 64 in an engaged position.

FIG. 67 is a close-up cross-sectional view of the insertion tool of FIG. 64 in a retracted position.

DETAILED DESCRIPTION OF THE INVENTION

As required, detailed embodiments are disclosed herein; however, it is to be understood that the disclosed embodiments are merely examples and that the systems and methods described below can be embodied in various forms.

Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Implants of the disclosure allow continuous expansion and retraction within a range of expansion. Lordosis of certain embodiments of implants herein can be custom tailored to fit the anatomy of a specific patient. Additionally, implants of the disclosure enable distraction of vertebral bodies to a desired height, but can also be collapsed and repositioned, as therapeutically indicated for the patient.

Figure 1:
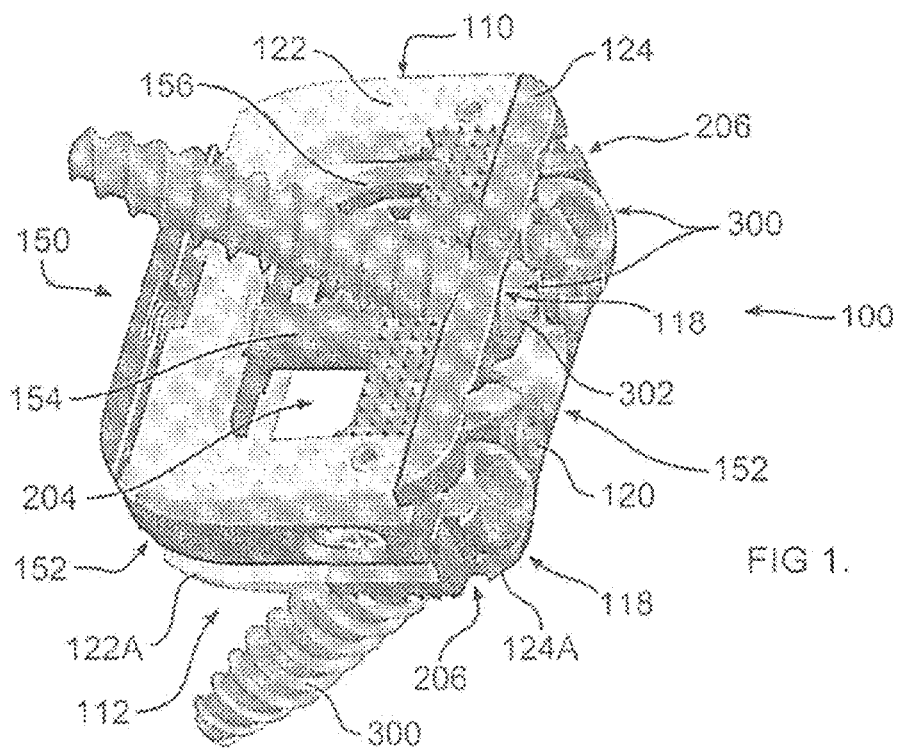
FIG. 1 depicts an implant of the disclosure, together with three mounted bone screws.
Figure 2:
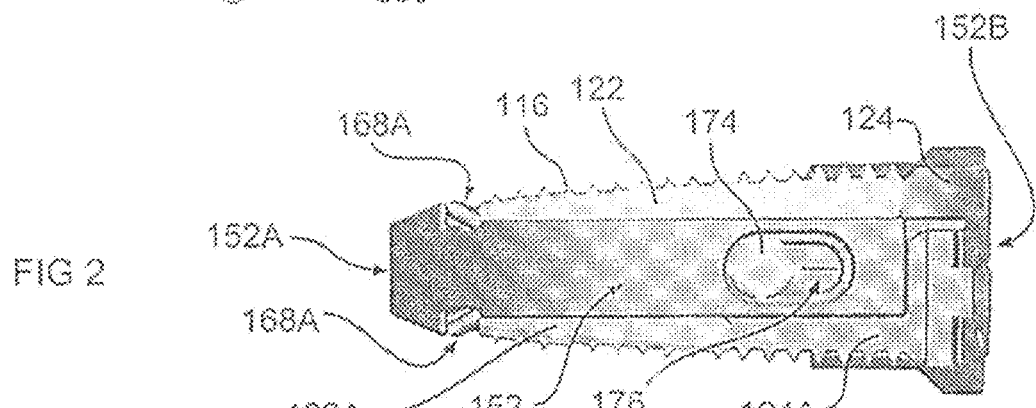
FIG. 2 depicts the implant of FIG. 1, in a compressed or reduced height configuration.
Figure 3:
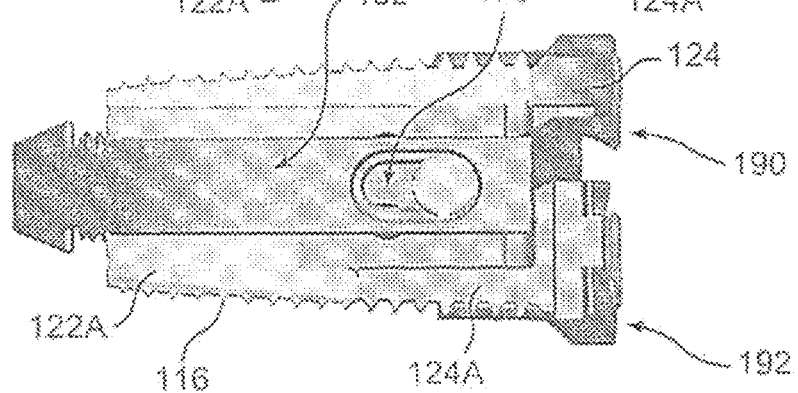
FIG. 3 depicts the implant of FIG. 1, in an expanded or increased height configuration.
Figure 33:
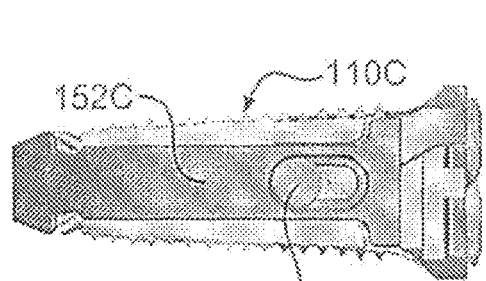
FIG. 33 depicts a side view of an alternative implant in accordance with the disclosure, in a reduced height configuration.
Figure 34:
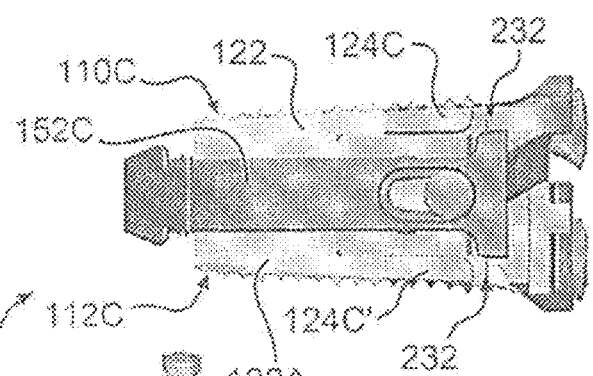
FIG. 34 depicts the implant of FIG. 33, in an expanded height configuration.

With reference to FIGS. 1-3, implant or implant 100 is operative, when positioned between adjacent bones of a joint, such as for example vertebrae 10, 12 (shown in FIG. 11), to stabilize a joint formed by adjacent vertebrae. Implant 100 has a collapsed state or height, illustrated in FIG. 2, and an expanded state or height, illustrated in FIG. 3. Implants 100 of the disclosure may be inset into the intervertebral disc space at a collapsed height, and then expand axially (superior/inferior) to restore height loss in the disc space. The implant provides distraction as well as achieves optimal height restoration. When inserted in a collapsed state, implants 100 reduce impaction to tissue in the joint space during insertion, and form the least visually blocking or obstructing profile.

Implant 100 includes two separable endplates 110, 112. A surface 114 of an endplate 110, 112 can be provided with teeth or other projections 116 which can penetrate body tissue to reduce a likelihood of migration of implant 100 after implantation. Implant 100 is further secured with one or more bone screws 300, which pass through bone screw socket 118 within implant 100, and into body tissue of the patient. In the embodiment illustrated in FIGS. 1-3, three sockets 118 for three bone screws are provided, the bone screws 300 further retained in connection with implant 100 by blocking fasteners 120. Bone screw 300 can be a polyaxial screw, and sockets 118 correspondingly shaped, whereby bone screw 300 may be inserted into body tissue at an optimal angle with respect to implant 100, whereby optimal purchase may be obtained, or certain body tissue may be avoided.

Endplates 110, 112 are moveably connectable to an actuator 150 operable to change a relative relationship of endplates 110 and 112. Actuator 150 includes a frame 152 rotatably supporting an actuator screw 154, and a moveable carriage 156. As actuator screw 154 rotates within frame 152, carriage 156 slides within frame 152, driven by cooperation between threads 158 (FIG. 8) upon actuator screw 154, and mating threads 160 within carriage 156. In the embodiment of FIGS. 1-3, endplates 110 and 112 are formed in two connected portions, including a portion 122, 122A which can be polymeric, and a portion 124, 124A, which can be metallic. The portions are joined in the embodiment shown by screws 162, although other methods of combining the two connected portions 122, 124 or 122A and 124A may be used, including a dovetail connection, or adhesive, possibly in combination with each other, or with endplate connector screws 162. Metallic portions 124, 124A can provide greater strength for portions of implant 100 which are under relatively greater stress, for example portions through which a fastener may pass to anchor implant 100 within the body. While portions 122, 122A, 124, 124A are described as polymeric or metallic, it should be understood that other materials may be used, and that the portions can be of dissimilar materials.

With reference to FIG. 2, it may be seen that implant 100 is in a compressed state, having a lower height relative to an expanded state, as shown in FIG. 3. A functioning of device 100 may be best understood with reference to FIGS. 9-10, which correlate with FIGS. 2-3, respectively, but which present a simplified view having certain elements eliminated or exaggerated, to ease understanding. Endplates 110 and 112 are provided with ramped channels 164, 164A, and an open ramp 166, 166A, sized to slidingly receive ramps 168, 168A and 170, 170A disposed upon carriage 156. While two mating channels and ramps are illustrated for each endplate 110, 112, it should be understood that one, or more than two, sets of channels and or ramps may be provided. Further, channels 164, 164A may alternatively be formed as ramps. However, a channel can operate to enable a reduction of height, having an opposing ramp face, whereby rotation of actuator screw 154 in an opposite direction to expansion can drive endplates 110, 112 together, for example when pressure from body tissue is insufficient to collapse endplates 110, 112. Additionally, at least one channel can operate to foster the maintenance of a connection between carriage 156 and an endplate 110, 112.

Carriage 156 is supported by frame 152 by lateral engagement means, in this embodiment two support screws 174 engaged with carriage 156, and passable through respective channels 176 formed in frame 152. Distal end 172 of actuator screw 154 provides additional support for carriage 156. Actuator screw 154 is supported by a set screw 178, which passes through and is rotatably supported within frame 152.

An actuator access port 180 permits passage of a tool, for example a hex driver (not shown), into engagement with a proximal end 182 of actuator screw 154. As actuator screw 154 is turned, distal end 172 bears against a thrust washer 184, and an end portion of frame 152. As actuator screw 154, carriage 156 is driven along actuator screw by interaction of threads 158 and 160. As carriage 156 moves, endplates 110, 112 are urged to move along ramps 168, 168A and 170, 170A, moving relatively apart, and increasing a height of implant 100. Endplates 110, 112 are prevented from moving together with carriage 156 by abutting against an end portion 186 of frame 152. In a given orientation, one of endplate 110 and 112 is an upper endplate with respect to an orientation in a standing patient. However, implant 100 may, in some embodiments, be implantable in either of opposite orientations, and therefore designations of upper and lower are provided for ease of understanding, only. It should be understood that only one of endplate 110, 112 may be moveable with respect to the other. For example, in one embodiment, ramps 168A, 170A may not be provided, and endplate 112 may be attached to frame 152.

FIG. 11 illustrates an implant 100 of the disclosure implanted between adjacent vertebrae 10, 12. Frame 152 defines a distal or leading end 152A which is inserted first into the body, and a proximal or trailing end 152B which passes last into the body, the distal and proximal ends defining a longitudinal axis extending therebetween. Implant 100 can be inserted into the body, and into a position between vertebrae, using minimally invasive methods, for example using a small incision, and implant 100 may be passed through a cannula or other structure which maintains a pathway through body tissue. Implant 100 may be inserted into the spinal column through any approach, including anterior, anterolateral, lateral, or posterolateral. A portion of the disc annulus, and nucleus pulposus may be removed in order to form a space into which implant 100 may be inserted. When implant 100 is in a compressed, or reduced height configuration, dovetail guides 200, 202 can be provided to foster maintenance of a relative orientation of upper and lower endplates during insertion or removal of device 100. Dovetail guides 200, 202 further stabilize endplates 110, 112 during expansion, and when implant 100 is expanded. Dovetail guides 200, 202, can have the form of a tongue and groove configuration, or other sliding mating configuration, with ends of ramps 168, 168A, for example.

Implant 100 can be inserted configured to have a lower height profile, as shown in FIG. 2, whereby an extent of distraction of body tissue may be reduced during insertion. Moreover, to the extent that implant 100 is used to open a pathway towards an implantation site, trauma to adjacent tissue is reduced relative to inserting an implant having a final height profile. Once implant 100 is positioned between adjacent vertebrae, actuator screw is rotated by a tool. The tool may be positioned entirely within the body, or can extend from in interior of the body to outside the body, for example having a driving tip at one end and having a handle at an opposite end, with a shaft extending into the body between each end.

Once actuator screw 154 has been rotated to separate endplates 110, 112 a desired amount, the tool is removed. At this point, actuator screw 154 may be secured in place, for example using a mechanical block, or an adhesive, to prevent unintended rotation of actuator screw 154. As carriage 156 is slideably moved by rotation of actuator screw 154, a ramp 166, 166A or a ramped surface of channel 164, 164A of at least one of endplate 110, 112 slides against at least one ramp 168, 168A, 170, or 170A of carriage 156, to cause the endplate to move along an axis transverse to the longitudinal axis of the frame, to increase a height of the implant. Rotation of actuator screw 154 in an opposite direction causes movement along an axis transverse to the longitudinal axis of the frame to decrease a height of the implant.

Polymeric insets, or a polymeric square nut, for example PEEK, can be provided, engageable with threads 158 or other portion of actuator screw 154, to provide additional friction to prevent height loss under load, particularly under cyclic loading. Similarly, once bone screws 300 have been inserted, blocking elements 120 may be rotated to extend over an end of bone screw head 302, preventing screw 300 from backing out. A similar mechanical block (not shown) may be provided for actuator screw 154.

With reference to FIGS. 1-3, 5-8, it may be seen that a socket 118 for a polyaxial screw head 302 can be formed entirely within one of upper or lower endplate 110, 112, or may be formed partially within each of endplate 110 and 112, whereby when implant 100 has been expanded to a final height, the proportions of an interior of socket 118 are correct or substantially correct for retaining screw head 302. For example, in FIG. 8, metallic portion 124 forms an upper portion 190 of socket 118, and mating metallic portion 124A forms a lower portion 192 of socket 118. In the embodiment illustrated in the figures, there are three sockets 118, and all are formed of upper and lower portions. However, there may be more or fewer sockets 118, and one or more sockets may be formed entirely in an upper or lower endplate.

In an embodiment, implant 100 of the disclosure provides an actuator that translates relative to the body by means of a threaded actuator screw 154. Ramps 168, 168A and 170, 170A on a carrier 152 mate with channels 164, 164A, and or ramps 166, on endplates 110, 112. Linear translation of carriage 156 causes endplates 110, 112 to expand implant 100 along an S/I axis with respect to the body. There can be dovetail guides that capture endplates 110, 112 when collapsing the implant.

Assembly screws 162 fasten endplates made of dissimilar materials, for example PEEK polymeric portions 122, 122A to Titanium metallic portions 124, 124A. A dovetail and press fit design can be used to connect the dissimilar endplate portions. A PEEK bushing or washer 184 is used between the threaded actuator screw 154 and frame 152 to minimize friction during expansion of implant 100. Support screws 174 and channels 176 cooperate to form side or lateral stabilizers, and set screw 178 supports a nose or leading end of carriage 156. Additionally, cooperating slots and projections (not shown) in carriage 156 and frame 152 can be provided for further relative guidance and stability.

In one embodiment, three bone screws 300 are used to provide fixation into adjacent vertebral bodies, two screws 300 passing through implant 100 and into one vertebra, and one screw 300 passing through implant 100 into another vertebra, although other combinations may be used. Bone screws 300 can have spherical or otherwise curved heads, facilitating insertion at a desired angle, or may be provided to mate with socket 118 in a fixed orientation, particularly depending on a diameter of a neck portion of screw 300. Cam style blocking fasteners 120 can be used to block bone screws 300 from backing out after being inserted.

Implants of the disclosure enable a continuous expansion and retraction over a range of displacements according to predetermined dimensions of a specific implant 100 design. This provides the ability to distract vertebral bodies to a desired height, but also to collapse the implant 100 for repositioning, if therapeutically advantageous for the patient. Endplates 110, 112 may be shaped to form planes or surfaces which converge relative to each, to provide for lordosis, and can be provided with openings, forming a graft chamber 204 through the openings and between the respective openings through which bone may grow, and into which bone graft material may be placed. Implant 100 may be used to distract, or force bones of a joint apart, or may be used to maintain a separation of bones created by other means, for example a distractor.

Implant 100 may be fabricated using any biocompatible materials known to one skilled in the art, having sufficient strength, flexibility, resiliency, and durability for the patient, and for the term during which the device is to be implanted. Examples include but are not limited to metal, such as, for example titanium and chromium alloys; polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material.

Portions or all of the implant may be radiopaque or radiolucent, or materials having such properties may be added or incorporated into the implant to improve imaging of the device during and after implantation.

For example, metallic portions 124, 124A of endplates 110, 112 may be manufactured from Titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Polymeric portions 122, 122A may be manufactured from ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of implant 100. For example, polymeric portions 122, 122A can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Implants of the invention may also be provided with an overall angular geometry, for example an angular mating disposition of endplates 110, 112, to provide for a natural lordosis, or a corrective lordosis, for example from 0° to 12°, or from 0° to 6° for a cervical application, although much different values may be advantageous for other joints. Lordotic angles may also be formed by shaping one or both of plates 110, 112 to have relatively non-coplanar surfaces. Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Implants 100 may be implanted within any level of the spine, and may also be implanted in other joints of the body, including joints of the hand, wrist, elbow, shoulder, hip, knee, ankle, or foot.

In accordance with the invention, a single implant 100 may be used, to provide stabilization for a weakened joint or joint portion. Alternatively, two, three, or more implants 100 may be used, at a single joint level, or in multiple joints. Moreover, implants 100 may be combined with other stabilizing means.

Additionally, implant 100 may be fabricated using material that biodegrades in the body during a therapeutically advantageous time interval, for example after sufficient bone ingrowth has taken place. Further, implant 100 is advantageously provided with smooth and or rounded exterior surfaces, which reduce a potential for deleterious mechanical effects on neighboring tissues. In some embodiments, the implant 100 is provided with teeth and is blasted thereafter to roughen the surface, thereby helping to provide enhanced surfaces for bone growth.

Any surface or component of the invention may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, implant 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position implant 100 may be performed through an Anterior, Anterolateral, Posterolateral, and/or Lateral approach.

In a typical embodiment, implant 100 has a uncompressed height, before insertion, of 12 to 18 mm, and may advantageously be provided in cross-sections of 23×32 mm, 26×38 mm and 26×42 mm, with 4, 8, 12, or 16 degree lordotic angles, although these are only representative sizes, and substantially smaller or larger sizes can be therapeutically beneficial. In other embodiments, the implant 100 can have a height between 8-21 mm and footprints of 25×31, 26×34, 39×39, with 8, 15 and 20 degree lordotic angles. In one embodiment an implant 100 in accordance with the instant disclosure is sized to be inserted using an MIS approach (a reduced incision size, with fewer and shorter cuts through body tissue).

Implant 100 may advantageously be used in combination with other known or hereinafter developed forms of stabilization or fixation, including for example rods and plates.

Referring now to FIGS. 13-18, implant 100 can be insert it into the intervertebral disc space at a collapsed height, and then expand it to restore the disc space height. Implant 100 provides distraction as well as achieves optimal sagittal balance. As discussed, there are multiple methods and approaches by which implant 100 can be inserted. FIGS. 14-18 illustrate one possible method and approach of the disclosure. While a series of numbered steps are described, it should be understood that there can be numerous other steps pertaining to the procedure, and that the steps described emphasize useful steps in the deployment of implant 100 of the disclosure.

Step 1: Approach—An approach to the desired section of the spine is performed using surgical instruments such as scalpels and retractors, for example using minimally invasive techniques.

Step 2: Preparation—Disc preparation instruments can be used to remove disc material and expose the disc space, for example using rongeurs and other suitable instruments (not shown), to create a disc space 14.

Step 3: Trialing—As may be seen in FIG. 14, trialing for implant footprint, height and wedge angle is performed to indicate which size or type of implant 100 is to be used. An expandable trial, static trials, or a combination of each may be used. In FIG. 14, trial implant 320 is trial fit using trial insertion tool 400.

Step 4: Insertion—Graft material or other therapeutically beneficial material is packed into graft chamber 204 of the selected implant 100 when it is collapsed or partially expanded. As may be seen in FIG. 15, implant 100 is inserted into disc space 14 using insertion tool 410. Tool engagement formations 206 are provided on opposite sides of frame 152 or one of endplate 124 or 124A, as can be seen in FIG. 1. Tool arms 412 securely and releasably engage tool engagement formations 206, and align an expansion driver 414 with actuator screw 154.

Step 5: Expansion—In FIG. 16, implant 100 is expanded, as described herein, by turning actuator screw 154 using expansion driver 414. After expansion, additional bone graft material can be packed through graft portals 208 into the central graft chamber 204 using a bone funnel 440 (FIG. 40). A push rod (not shown) can be used for driving graft material through funnel 440.

Step 6: Hole Preparation—Bone screw pilot holes can be formed into one or more adjacent vertebrae, prepared using, for example, awls, drills and or taps. Multiple pilot holes can be prepared first, or pilot holes can be prepared one at a time, before the insertion of each screw 300. During any of the steps herein, imaging can be carried out to avoid damage to adjacent tissue.

Step 7: Screw Insertion—In FIG. 17, bone screws 300 are inserted using bone screw driver 416. To facilitate access for bone screw driver 416, expansion driver 414 may be withdrawn from insertion tool 410. After bone screws 300 are inserted, they can be blocked from backing out using blocking element 120. Lagging of the vertebral bodies can be performed before or after the bone screws are locked. Fluoroscopy or other imaging can be used to confirm final placement. Imaging can also be used at any of the steps to confirm work performed. Further, bone screw hole preparation and bone screw 300 insertion can be carried out prior to implant 100 expansion, to promote anchoring of the implant during expansion. In FIG. 18, an expanded implant 100 can be seen between vertebrae, secured by bone screws 300. The foregoing method provides a customized fit using implant 100, and minimizes disruption to patient anatomy.

Referring now to FIGS. 19-32, an alternative implant 100B of the disclosure has a shorter actuator screw 154B relative to actuator screw 154 of implant 100 of FIG. 1. Actuator screw 154B engages a proximal end of carriage 156B, and does not pass through graft portal 208B. A compact actuator frame 212 includes a screw bearing 210, and upper and lower tabs 214, 216, respectively. Endplate slots 218, 220 within endplates 110B and 112B slidingly receive upper and lower tabs 214, 216. In this manner, actuator screw 154B is rotatably fixed along a longitudinal axis with respect to endplates 110B and 112B, the longitudinal axis indicated in FIG. 19 to extend between distal ("D") and proximal ("P") ends. Endplates 110B, 112B can slide upon collar tabs 214, 216 to mutually separate to form an expanded configuration of implant 100B. Actuator screw 154B can be rotatably retained within compact actuator frame 212, so that carriage 156B can be pushed or pulled in threaded engagement with actuator screw 154B, without an axial displacement of actuator screw 154B. This can be accomplished, for example, by a clip or other cooperative engagement between compact actuator frame 212 or bearing 210, and actuator screw 154B, or a blocking element (not shown) partially covering an end portion of actuator screw 154B. In an embodiment, tabs 214 and 216 form a dovetail connection with endplate slots 218, 220.

It should be understood that implant 100 may identified with a suffix herein, for example 100B, 100C, 100D, 100E, to indicate embodiments illustrating various features of the disclosure. In consideration of the impracticality of illustrating and describing every possible permutation of features, it should be understood that, where logical, features of the various implants may be substituted among the implants. Thus, all of the implants may collectively be referred to as implant 100, unless a specific reference is made to a feature illustrated by a particular embodiment.

Actuator screw 1546B threadably engages carriage 156B at threads 160B, whereby rotation of screw 154B causes carriage 156B to move towards or away from compact actuator frame 212. Carriage 156B has ramps 168, 168A and 170, 170A, which engage corresponding endplate ramps 164, 164A, 166, 166A as described with respect to implant 100. As actuator screw 154B is rotated, carriage 156 translates with respect to endplates 110B, 112B. As a result, carriage ramps 168, 168A and 170, 170A slide against endplate ramps 164, 164A, 166, 166A, causing endplates 110B, 112B to mutually separate. In an embodiment, carriage 156B is polymeric at threads 160B, and an interference fit is formed between actuator screw 154B and threads 160B, whereby sufficient friction is created to resist unintended rotation of actuator screw 154B, with a consequential change in height of implant 100B.

Frame 152 slidingly bears against frame support edges 224 extending along endplates 110B, 112B, and is slidingly connected to carriage 156B by carriage support screws 174. In this manner, carriage 156B is laterally supported, and inhibited from rotational movement, but may move longitudinally along a path defined by carriage support channel 176 and actuator screw 154B. Additionally, channels or dovetail guides 200, 202 in endplates 110B, 112B receive mating end portions 200A, 202A of carriage ramps 168, 168A, 170, 170A, to further guide and stabilize endplates 110B, 112B.

FIGS. 19-32 further illustrate an alternative blocking element 120B, which, as with other of the various alternative elements herein, may be combined with other implant embodiments herein. Element 120B forms an sliding block 226 within a block groove 228, block 226 and block groove 228 forming a dovetail or other sliding mating engagement, wherein block 226 is confined to movement along a path defined by block groove 228. Once bone screw head 302 is fully seated within bone screw socket 118, block 226 may be rotated partially out of engagement with block groove 228 to a position over bone screw head 302, thereby blocking a movement of bone screw 300 out of engagement with bone or body tissue. In the embodiment shown, two blocking elements 120B are illustrated, wherein a tool having two end portions (not shown) can be inserted adjacent each block 226, and the tool rotated to move both blocks into a blocking position. Accordingly, blocks 226 together form substantially concentric arcs pivoting about the same or close axes.

Implant 100B is configured to facilitate the insertion of graft material or other therapeutic material through one or more of bone screw socket 118 into graft chamber 204 formed by openings within endplates 110B, 112B, and carriage 156B. After the material is inserted, bone screws 300 may then be inserted into socket 118 and fastened to body tissue as otherwise shown and described herein. A bone funnel 440 (FIG. 40) may be used to urge material into graft chamber 204. Alternatively, once implant 100B is expanded, materials may be inserted into an endplate gap 230 formed by a separation of endplates 110B, 112B, as may best be seen in FIGS. 30 and 32, which are cross-sections taken through compact actuator frame 212, and upper and lower tabs 214, 216.

It should be understood that endplates of the disclosure, in all embodiments, may be formed of a unitary material, as illustrated in FIGS. 19-32 for example, or multiple materials, as illustrated in FIGS. 1-6 for example. Accordingly, endplates 110B, 112B may be formed of multiple materials, for example titanium for a proximal, bone screw engaging portion, and UHMWPE for a distal, bone engaging portion. Further, endplates 110B, 112B may be provided with teeth or other projections, to positively engage body tissue and reduce a likelihood of undesired migration of implant 100B.

With reference to FIGS. 33-40, a spacer implant 100C includes frame 152C which forms a dovetail engagement with upper and lower endplates 110C, 112C. In this manner, endplates 110C, 112C are further stabilized throughout a range of expansion of implant 100C. As may be seen in FIG. 36, a cross section of endplate portion 124C illustrates frame support channel 232 of endplate portion 124C is shaped to slidingly retain frame extension guide 234 of frame 152C (also visible in FIGS. 44-45). It should be understood that an inverse configuration can be created, wherein a channel is formed in frame 152C and an extension is formed from endplate portion 124C. Similar channels and extensions can be formed on opposing sides of frame 152C, as illustrated, with a frame support channel 232 formed in lower endplate portion 124C', as well. In an embodiment, frame 152C can form an extended region 238 along all or part of the dovetail engagement area of frame support channel 232 and extension guide 234. For example, frame 152C can extend in superior and inferior directions to extend from near an outer surface of endplate 110C to near an outer surface of endplate 112C, or may extend over a lesser distance. Channel 232 and extension guide 234 are illustrated as transverse to an A-P or longitudinal axis of implant 100C. In an alternative embodiment, channel 232 and guide 234 are disposed at a non-transverse angle with respect to the longitudinal axis.

Figure 35:
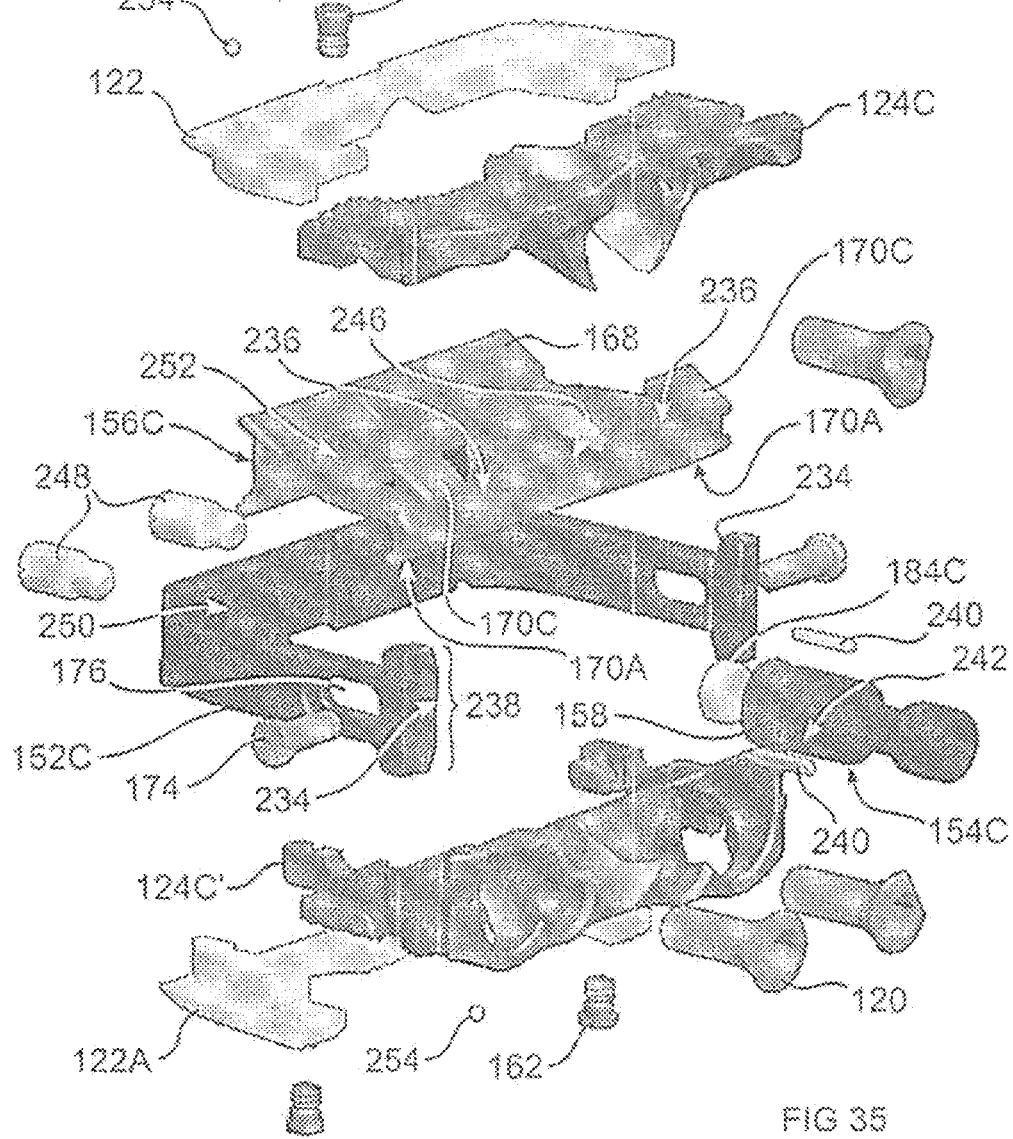
FIG. 35 depicts an exploded view of the implant of FIG. 33.

With reference to FIGS. 35 and 37, carriage 156C includes one or more graft chamber portals 236, providing access from a exterior to a proximal end of implant 100C into graft chamber 204, after implant 100C is implanted within the body. Carriage 156C includes two portals 236 specifically formed to admit the passage of graft or other therapeutic materials, however one or more than two portals 236 can be provided. In the embodiment illustrated, graft chamber portals 236 are formed within a portion of carriage ramp 170, although other portions of carriage 156C may be shaped or opened in a like manner. A bone funnel 440 may be used to direct material through one or more of graft chamber portal 236.

As can be seen in FIG. 35, actuator screw 154C includes actuator screw bearing 184C and lateral screw bearings 240, provided to promote smooth rotation of actuator screw 154C. Bearing channels 242 within actuator screw 154C can be provided to maintain an orientation of lateral screw bearings 240 within screw guide 246 of carriage 156C. In an embodiment, an interference fit is formed between lateral screw bearings 240 and screw guide 246, to prevent unintended rotation of actuator screw 154C. To further stabilize carriage throughout at least a portion of its range of motion, stabilizing posts, screws, or pins 248 can be provided, connected to frame 152C, for example within frame pin bore 250 by threads, adhesive, or an interference fit, and slideably engageable within pin bores 252 within carriage 156C. Alternatively, pins 248 can be affixed to carriage 156C, and can slide within frame pin bores 152C. In an embodiment, As can be seen in FIGS. 35 and 38-39, one or more radiographic markers 254 are positioned within implant 100C, for example within radiotransparent portions of implant 100C, or any other radiotransparent portion of the various embodiments herein. For example, a radiographic marker can be positioned within polymeric endplate portion 122, 122A, so that an expanded or contracted position thereof may be positively ascertained using imaging. As may be seen in FIG. 39, radiographic markers 254A, 254B are oriented to be aligned with an end of carriage ramps 168, 168A, which in this embodiment are radiopaque, only when implant 100C is fully expanded. To indicate an extent of expansion, one or more radiopaque markers 254 can be positioned with respect to frame 152, carriage 156, or any other portion of implant 100 which does not move together with an endplate 110, 112, and which is radiopaque, or which is similarly configured with a radiopaque marker 254.

FIG. 40 illustrates a bone funnel 440 useable with implants 100, 100B, 100C, 100D, 100E (collectively, herein, 100) of the invention. An output aperture 442 is placed proximate an opening into an open area within implant 100, for example graft chamber 204. Bone graft material, and or other therapeutic agents, are collected within including for example bone growth factors, antimicrobial agents, or other therapeutic is placed into widened input chamber 444, and then pushed down pipe 446 with a driver, for example a rod (not shown). A pipe connector 448 can be provided, sized to correspond to graft chamber portal 236. Driven bone graft material is passed into an interior of implant 100, where it may have its intended therapeutic benefit upon contacting body tissue of at least one vertebra.

In an embodiment, carriage ramps 168, 168A, 170, 170A can have differing ramp angles and or sizes, wherein endplate ramps 166, 166A have corresponding profiles and sizes. For example, if ramps 168, 168A are shorter than ramps 170, 170A, expansion will occur at a greater rate along a proximal side of implant 100, and in this manner an angular orientation of the spine, for example lordosis, may be corrected. Similarly, ramps 170, 170A can be shorter than ramps 168, 168A. Alternatively, one side of ramp 168, 168A can be shorter than another side of ramp 168, 168A, with a corresponding difference along ramps 170, 170A. In this manner, a sideways orientation of the spine, for example Scoliosis, may be corrected.

Figure 41:
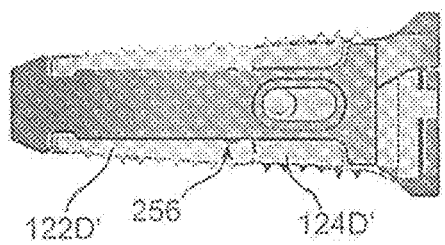
FIG. 41 depicts an alternative implant of the disclosure, including hinged endplates, in a reduced height configuration.
Figure 42:
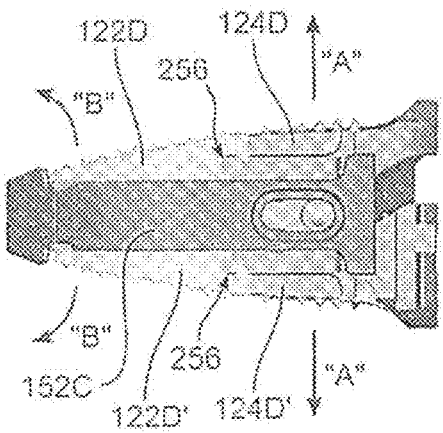
FIG. 42 depicts the implant of FIG. 41, in an expanded configuration.
Figure 43:
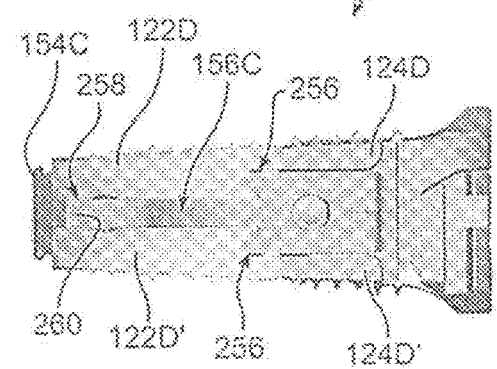
FIG. 43 depicts the implant of FIG. 41, with a frame portion removed.

FIGS. 41-43 illustrate an alternative implant 100D of the disclosure, which pivots proximate ends of endplates 110D, 112D, providing both axial translation, as indicated by arrows "A", and pivoting, as indicated by arrows "B". Axial translation is maintained using frame 152C, together with frame extension guide 234 and frame support channel 232, as described with respect to implant 100C. However, an endplate pivot 256 is formed between endplate portions 122D and 124D, and between endplate portions 122D' and 124D'. FIG. 43 illustrates implant 100D with frame 152C removed, illustrating a endplate hinge 258 formed between endplate portions 122D and 122D'. Connected in this manner, endplate portions 122D and 122D' pivot about endplate hinge 258, as well as endplate pivots 256. Accordingly, a height of implant 100D at a distal end of implant portions 122D and 122D' is held constant, while a proximate end of implant portions 122D and 122D' translates axially with endplate portions 124D and 124D' to increase a height of implant 100D.

Implant 100D can be inserted into the intervertebral disc space at a collapsed height, and then expanded into lordosis to restore sagittal balance and height loss in the disc space. Implant 100D provides distraction as well as achieving optimal sagittal balance. Further, implant 100D reduces impaction to body tissue during insertion at a collapsed height, and gives a medical practitioner the capability to continuously adjust the lordotic angle of the supporting endplates to best fit the patient's anatomy and therapeutic needs.

Endplate pivot 256 is formed as mating circular portions of endplate portions 122D and 124D, and of endplate portions 122D' and 124D'. While one endplate portions forms an extension, and the other a receptacle, it should be understood that this configuration may be reversed.

Endplate hinge 258 is formed as a flexible connector 260 extending between endplate portions 122D and 122D'. In an embodiment, endplate portions 122D and 122D' are molded as a single part from a polymeric or other flexible material, thus forming a living hinge. In a further embodiment, a hinge is formed between endplate portions 122D and 122D' by any known means, including a barrel or flag hinge, or a hinge similar in style to endplate pivots 256. In an alternative embodiment, endplate hinge 258 is formed in connection with frame 152C.

By providing both axial and pivoting movement of endplate portions, implant 100D enables the formation of an alternative supporting structure, and in particular, a supporting structure with a convex conformity. This can be useful to correct particular spinal problems, including lordosis, for example.

Figure 44:
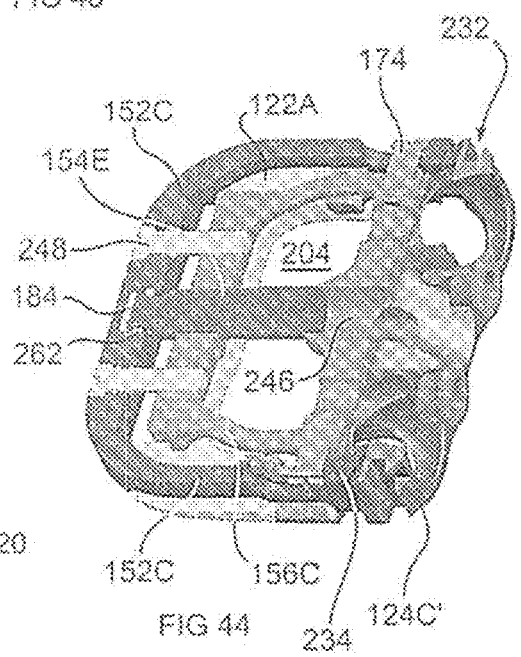
FIG. 44 depicts a cross section of an alternative implant of the disclosure, in perspective, having an elongate actuator screw.
Figure 45:
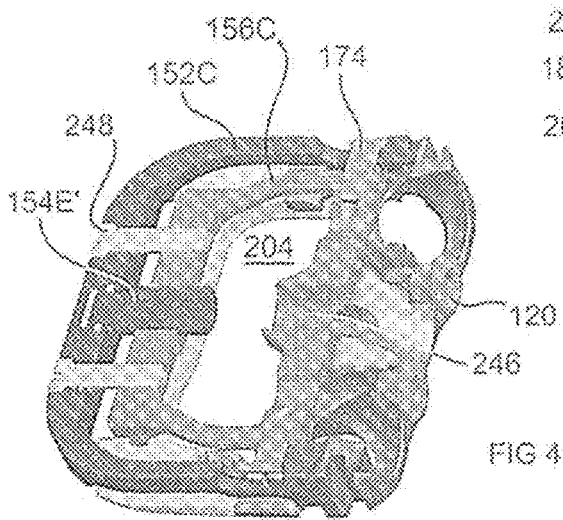
FIG. 45 depicts the implant of FIG. 44, having a shortened actuator screw.

With reference to FIGS. 44-45, which are cross-sections of an alternative implant 100E of the disclosure, it may be seen that actuator screw 154E is rotatably connected to frame 152E, for example using C-clip 262, as illustrated. An alternative method of rotatably securing actuator screw to frame 152E can include, for example, a leading set screw 178 (see, e.g. FIGS. 6, 6A) that freely spins relative to frame 152E, but is affixed to actuator screw 154E. An alternative method includes forming mating portions (not shown) upon frame 152E and screw 154E.

Further stability can be provided for carriage 156C through the use of stabilizing pins 248, frame pin bores 250, and pin bores in carriage 152C, as described with respect to implant 100C herein.

In a further embodiment, actuator screw 154E' is shorter than actuator screw 154E, and thereby reduces an obstruction of graft chamber 204. A tool can be passed through screw guide 246, and then through graft chamber 204, to engage actuator screw proximal end 182. Graft material can additionally be passed through screw guide 246, and placed within graft chamber 204. Bone funnel 140 can be used to pass materials through screw guide 246, and pipe connector can be adapted or replaced to best fit the dimensions of screw guide 246.

Figure 46:
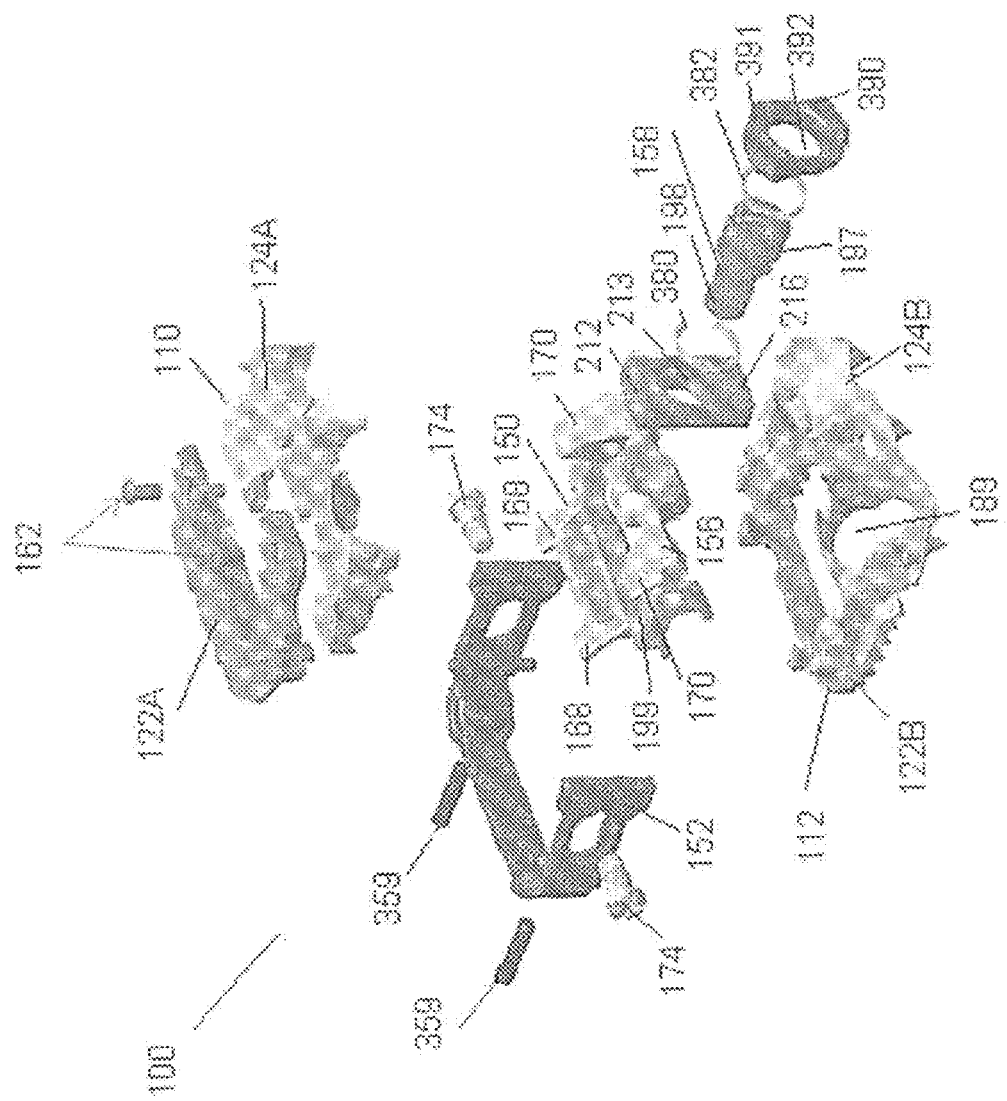
FIG. 46 depicts an exploded view of an alternative expandable implant including guide pins in accordance with embodiments of the present application.

FIG. 46 depicts an alternative expandable implant including guide pins in accordance with embodiments of the present application. The expandable implant 100 includes many features disclosed in prior embodiments, including a first endplate 110, a second endplate 112, a frame 152 for receiving an actuator 150 therein, and an actuator screw 154. In addition, the expandable implant 100 in FIG. 46 includes additional features, including guide pins 359, first and second compressible clips 380, 382 and a blocking mechanism 382.

As shown in FIG. 46, the expandable implant includes an upper or first endplate 110 and a lower or second endplate 112. The upper endplate 110 can be comprised of a first portion 122A and a second portion 124A that are operatively coupled together (e.g., via a fastener). In some embodiments, the first portion 122A comprises a polymeric portion, while the second portion 124A comprises a metallic portion. By having an endplate formed of a polymeric portion and a metallic portion, this advantageously provides an endplate that is both radiolucent and strong. The lower endplate 112 can be comprised of a first portion 122B and a second portion 124B that are operatively coupled together (e.g., via a fastener). In some embodiments, the first portion 122B comprises a polymeric portion, while the second portion 124B comprises a metallic portion. In other embodiments, the endplates 110, 112 can be formed of a single piece that is formed of either a polymer, such as PEEK, or a metal, such as titanium or cobalt-chrome. As in prior embodiments, the upper endplate 110 and the lower endplate 112 can include one or more bore holes for receiving bone screws therein. For example, as shown in FIG. 46, lower endplate 112 includes at least one bore hole 189 for receiving a bone screw therethrough for securing the implant 100 to an adjacent bone member.

A frame 152 for receiving an actuator 150 is positioned between the first endplate 110 and the second endplate 112. The frame 152 is configured to receive side support screws 174 through channels to secure the frame 152 to the actuator 150. In addition, one or more guide pins 359 are provided at a distal or leading end of the frame 152. The guide pins 359 are inserted through openings in the frame 152 and contact a surface of the actuator 150. By engaging the actuator 150, the guide pins 359 advantageously stabilize the actuator 150 such that it is not tilted during use.

The actuator 150 comprises a moveable carriage 156 having a first pair of upper ramped surfaces 170 connected to a second pair of upper ramped surfaces 168 via a bridge member 199. In some embodiments, the first pair of upper ramped surfaces 170 and the second pair of upper ramped surfaces 168 are inclined in the same direction (e.g., toward the distal or leading end of the actuator 150). The first and second pair of upper ramped surfaces 170, 168 are configured to engage corresponding angled or ramped surfaces of the first endplate 110, such that movement of the carriage 156 causes expansion of the implant 100. In some embodiments, a first pair of lower ramped surfaces extends downwardly from the first pair of upper ramped surfaces 170, while a second pair of lower ramped surfaces extends downwardly from the second pair of upper ramped surfaces. The first and second pair of lower ramped surfaces are configured to engage corresponding angled or ramped surfaces of the second endplate 112, such that movement of the carriage 156 causes expansion of the implant 100.

An actuator screw 154 can be provided to actuate the actuator 150. The actuator screw 154 comprises a head portion 197 and a shaft portion 198. The shaft portion 198 comprises threads for engaging a corresponding threaded portion of the actuator 150. Rotational movement of the actuator screw 154 in a first direction causes linear translation of the moveable carriage 156 of the actuator 150, thereby causing separation of the endplates 110, 112 and expansion of the implant. Rotational movement of the actuator screw 154 in a second direction opposite the first direction causes linear translation of the moveable carriage 156 of the actuator 150 in an opposite direction, thereby causing contraction of the endplates 110, 112.

Figure 47B:
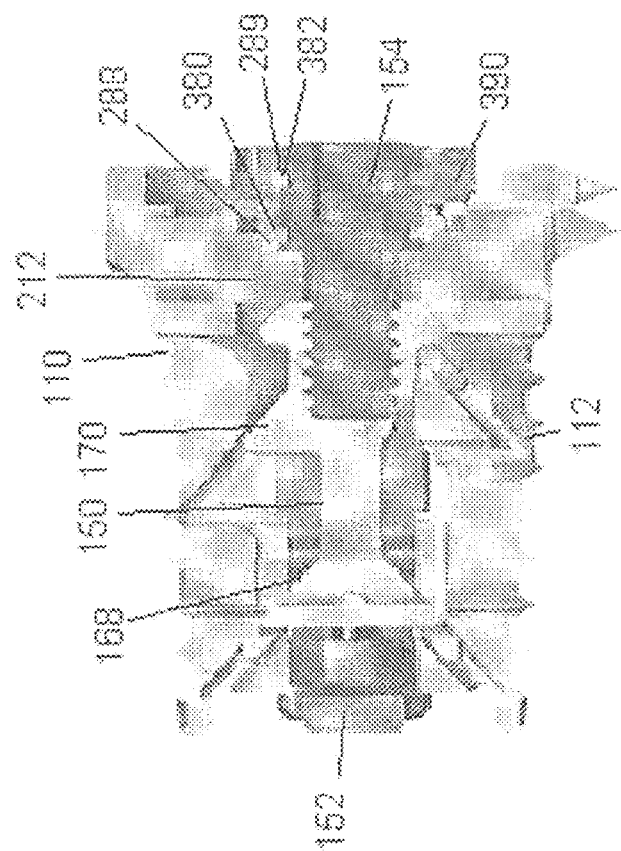
FIGS. 47A and 47B depict unexpanded and expanded configurations of the expandable implant in FIG. 46.
Figure 47A:
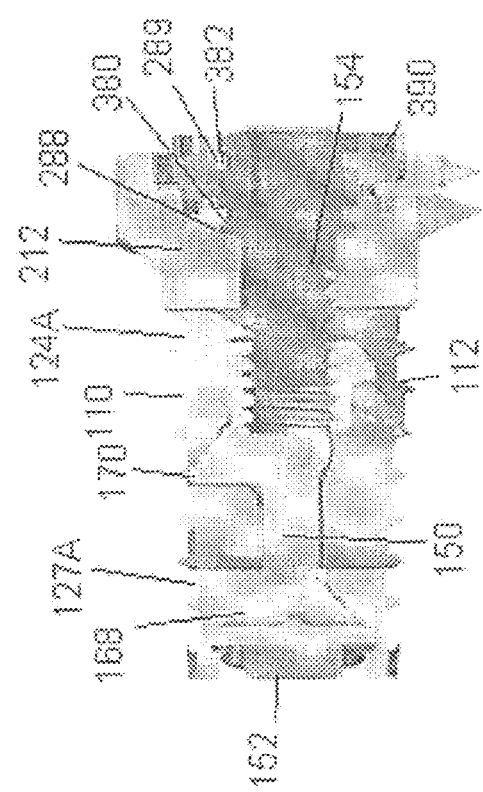

To retain the actuator screw 154 in the implant 100, an actuator frame 212 can be provided. The actuator frame comprises an upper tab portion 214 and a lower tab portion 216, and an opening 213 therebetween for receiving the actuator 150 therethrough. The upper tab portion 214 can be received in a slot in the first endplate 110, while the lower tab portion 216 can be received in a slot in the second endplate 112. To maintain the actuator 150 in the actuator frame 212, a first compression clip or "C-clip" locking mechanism 380 can be provided to secure the actuator 150 to the actuator frame 212. The C-clip 380 is configured to fit around a portion of the actuator 150, such as the head portion 197. In some embodiments, the C-clip 380 is retained within a recess or groove formed around the circumference of the actuator head portion. The C-clip 380 is advantageously configured to compress such that it can be trapped in a recess 288 in the actuator frame 212 (as shown in FIGS. 47A and 47B). This advantageously secures the actuator 154 within the actuator frame 212.

To prevent the bone screws from inadvertently backing out, a blocking mechanism 390 can be provided and attached via a C-clip 382. The blocking mechanism 390 comprises a body 391 having an opening 392 for receiving at least a portion of the head portion 197 of the actuator screw 154 therethrough. In some embodiments, a second compression clip or "C-clip" locking mechanism 382 can be provided to secure the blocking mechanism 390 to the actuator screw 154. As shown in FIGS. 47A and 47B, the C-clip 382 is configured to fit around the head portion 197 of the actuator screw 154. In some embodiments, the C-clip 382 can be received within a recess or groove formed in the head portion 197 of the actuator screw 154. The C-clip 382 is configured to compress until it reaches a recess 289 (shown in FIGS. 47A and 47B) in the blocking mechanism 390, thereby securing the C-clip 382 to the blocking mechanism 390.

FIGS. 47A and 47B show the implant 100 of FIG. 46 in unexpanded and expanded configurations, respectively. From these views, one can see the additional novel features, such as the first C-clip 380 and the second C-clip 382 retained in recesses 288, 289, thereby maintaining the components of the implant 100 in a secure connection.

In some embodiments, the implant 100 of FIG. 46 is sized and configured to be used in an anterior approach. In some embodiments, when assembled, the leading end of the implant 100 comprises a convex surface, while the trailing end of the implant 100 comprises a substantially flat surface. The leading end and the trailing end can be separated by curved arms, formed by side arms of the frame 152.

A method of insertion is now provided. After forming an incision in a patient and removing tissue from a disc space, a surgeon can insert the implant 100 through an anterior approach. The implant 100 can be inserted in an unexpanded configuration, as shown in FIG. 47A. Once the implant 100 has been inserted into the disc space, the implant 100 can be expanded by rotating or actuating the actuator screw 154 (e.g., via a driver). This causes translational movement of the carriage 156 with the ramps, thereby causing expansion of the implant 100. In some embodiments, prior to inserting and expanding the implant 100, bone graft material can be provided in a graft opening of the implant. In other embodiments, the implant 100 can include an opening that can receive bone graft therethrough after inserting the implant 100 in a disc space. In some embodiments, bone graft material can be inserted through the screw opening 189 (shown in FIG. 46) after the implant 100 is inserted into a disc space. In other embodiments, the implant 100 can be used in different approaches, including posteriorly or laterally.

FIG. 48 depicts an alternative expandable implant including endplates that are formed primarily of metal in accordance with embodiments of the present application. The expandable implant 100 includes many features disclosed in prior embodiments, including a first endplate 110, a second endplate 112, a frame 152 for receiving an actuator 150 therein, and an actuator screw 154. The expandable implant also includes guide pins 359 and compression C-clips 380, 382 as discussed with respect to prior embodiments.

As shown in FIG. 48, the first endplate 110 is a single-piece member formed of a metal. Likewise, the second endplate 112 is a single-piece member formed of a metal. In some embodiments, the first and second endplates 110, 112 are formed completely of a metal, as shown in FIG. 48. In other embodiments, the first and second endplates 110, 112 are formed primarily of a metal, but may have traces of other materials. Advantageously, by providing endplates that are formed primarily or completely of metal, this creates an implant having increased strength.

In some embodiments, the expandable implant 100 in FIG. 48 is sized and configured to be implanted anteriorly. In other embodiments, the expandable implant 100 can be inserted posteriorly or laterally.

Figure 50A:
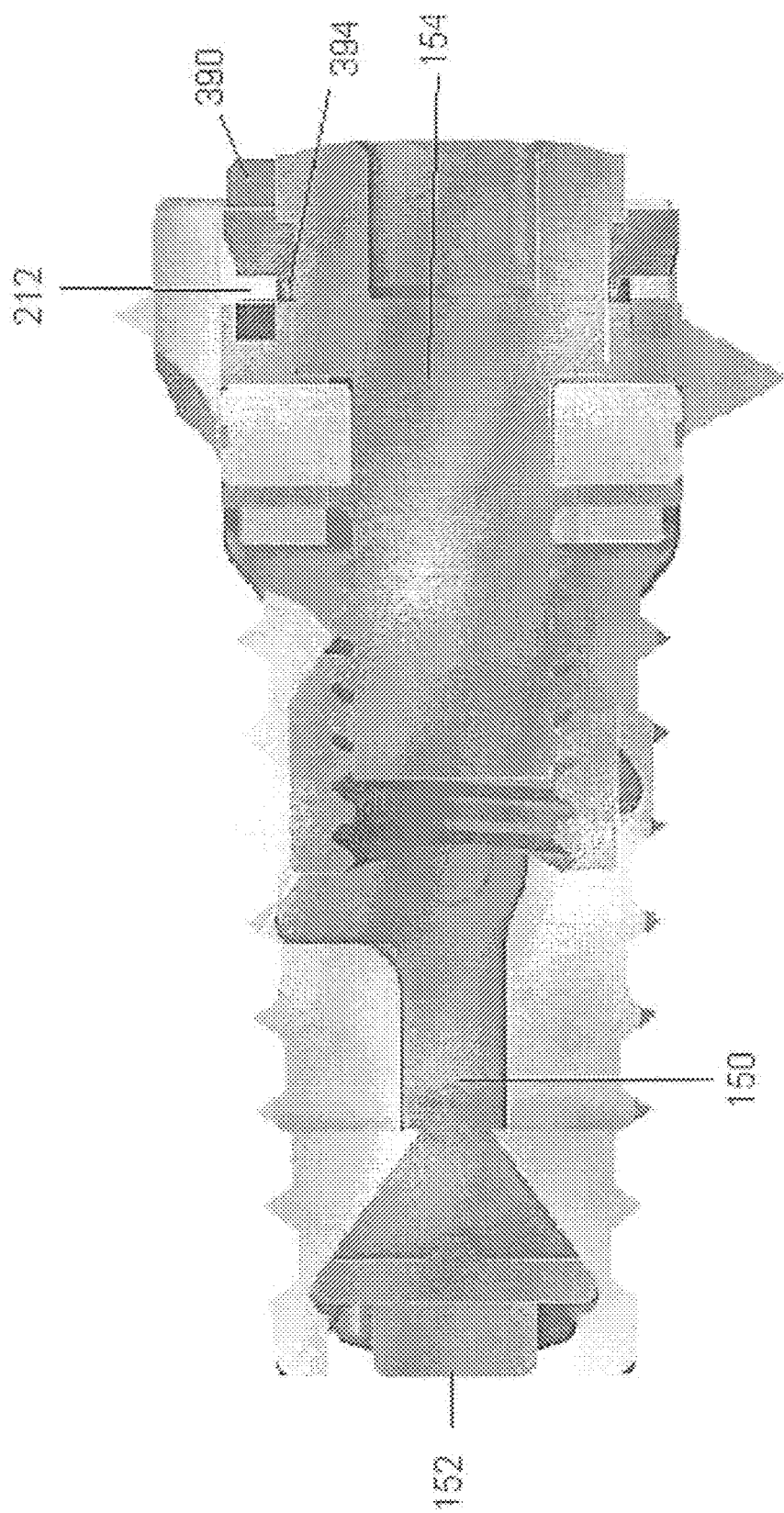
FIGS. 50A and 50B depict unexpanded and expanded configurations of an alternative expandable implant having an alternate means to capture the blocking mechanism in accordance with embodiments of the present application.
Figure 50B:
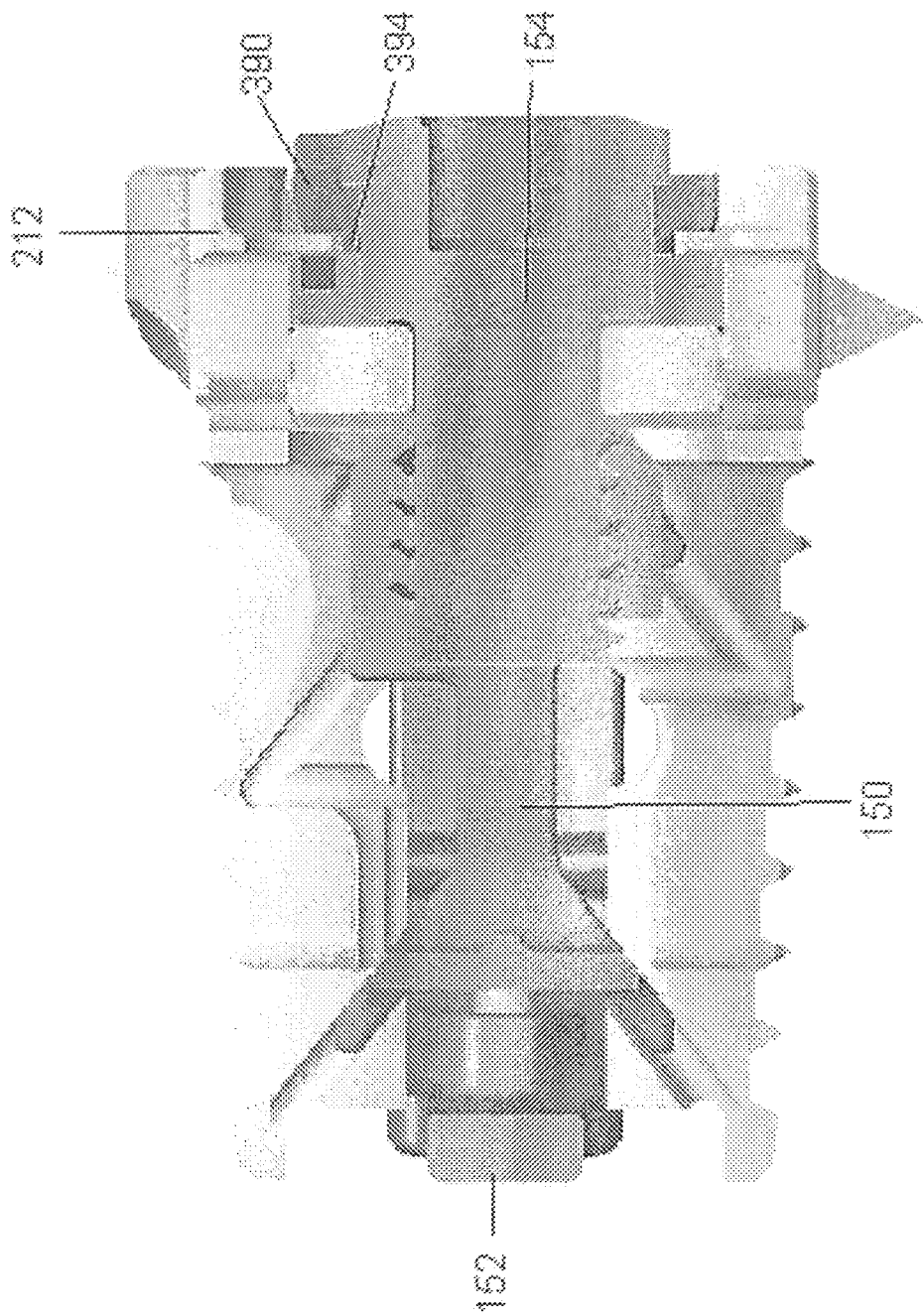

FIGS. 50A and 50B illustrate unexpanded and expanded configurations of an alternative expandable implant having an alternative means to capture the blocking mechanism in accordance with embodiments of the present application. The expandable implant 100 includes many similar features as prior embodiments, including a first endplate 110, a second endplate 112, a frame 152 for receiving an actuator 150, and an actuator screw 154. The implant 100 in the current embodiment, however, has a distinct blocking mechanism 390 that is not attached to the actuator screw 154 by a C-ring. Rather, the blocking mechanism 390 is captured between the actuator screw 154 and the actuator plate 212. The blocking mechanism 390 includes an extension portion 394 that can fit in a recess, groove or track formed in the actuator plate 212. As the actuator screw 154 is rotated and linearly translated, the actuator screw 154 pushed in the blocking mechanism 390 such that the extension portion 394 of the blocking mechanism 390 engages the track of the actuator plate 212, thereby securely capturing the blocking mechanism 390 within the assembly. In other embodiments, a compression C-ring can be optionally provided to retain the blocking mechanism 390 on the actuator screw 154, in addition to the engagement mechanism discussed herein.

FIG. 51 is an exploded view of an alternative implant in accordance with some embodiments. The implant 500 shares similar features as previous embodiments, including an upper endplate 510 and an opposed lower endplate 512. A frame 552 is positioned between the upper endplate 510 and the lower endplate 512. A moveable actuator 550 with one or more ramps is positioned within the body of the frame 552. The actuator 550 can be operably connected to the frame 552 via one or more support screws 574. A threaded actuator screw 554 can extend through the actuator 550. Rotation of the actuator screw 554 can cause linear translation of the actuator 550, thereby causing the upper endplate 510 and the lower endplate 512 to expand and separate away from one another. One or more fixation or bone members can then be received through each of the upper endplate 510 and the lower endplate 512, to thereby secure the implant 500 to adjacent bone members. One or more blocking elements 520 can be provided to reduce the risk of inadvertent back out of the bone members.

In the present embodiment, the upper endplate 510 is configured to include partial openings 513*a*, 515*a* and 517*a*. As shown in FIG. 53A, each of the partial openings 513*a*, 515*a* and 517*a* align and correspond with partial openings 513*b*, 515*b*, 517*b* in the lower endplate 512 to form first opening 513, second opening 515, and third opening 517. Each of these openings 513, 515, 517 is associated with at least one socket 518 for receiving a bone screw therein. In the embodiment shown in FIG. 51, a first socket 518 is associated with the partial opening 513*a* and a second socket 518 is associated with the partial opening 515*a*. Each of these sockets is designed to receive an upwardly angled bone screw therein. As shown in FIG. 51, as the upper endplate 510 moves, the partial openings 513*a*, 515*a*, and 517*a* move as well at the same rate, as they are part of the upper endplate 510. In some embodiments, the upper endplate 510 can be formed of a single material, such as a metal (e.g., titanium).

In addition, the upper endplate 510 is configured to include an upper lateral tool notch 519*a* on each side of the implant 500. The upper lateral tool notches 519*a* align and correspond with lower lateral tool notches 519*b* in the lower endplate 512, thereby forming tool notches 519. The tool notches 519 are capable of being gripped by an insertion tool to deliver the implant 500 to a surgical site. In some embodiments, other instruments other than insertion tools can be used to grip the notches 519.

In the present embodiment, the lower endplate 512 is configured to include partial openings 513*b*, 515*b* and 517*b*. As discussed above, as shown in FIG. 53A, each of the partial openings 513*b*, 515*b* and 517*b* align and correspond with partial openings 513*a*, 515*a*, 517*a* in the upper endplate 510 to form first opening 513, second opening 515, and third opening 517. Each of these openings 513, 515, 517 is associated with at least one socket 518 for receiving a bone screw therein. In the embodiment shown in FIG. 51, a third socket 518 is associated with the partial opening 517*b*. The socket is designed to receive a downwardly angled bone screw therein. As shown in FIG. 51, as the lower endplate 512 moves, the partial openings 513*b*, 515*b*, and 517*b* move as well at the same rate, as they are part of the lower endplate 512. In some embodiments, the lower endplate 512 can be formed of a single material, such as a metal (e.g., titanium).

In addition, the lower endplate 512 is configured to include a lower lateral tool notch 519*b* on each side of the implant 500. As discussed above, the lower lateral tool notches 519*b* align and correspond with upper lateral tool notches 519*a* in the upper endplate 512, thereby forming tool notches 519. The tool notches 519 are capable of being gripped by an insertion tool to deliver the implant 500 to a surgical site. In some embodiments, other instruments other than insertion tools can be used to grip the notches 519. One skilled in the art will appreciate that in some embodiments, the upper endplate is switched with the lower endplate. For example, a surgeon may use the implant in any configuration in a disc space, such that the lower endplate (shown in FIG. 52) can be viewed on top and the upper endplate (shown in FIG. 52) can be viewed on bottom.

Figure 52:
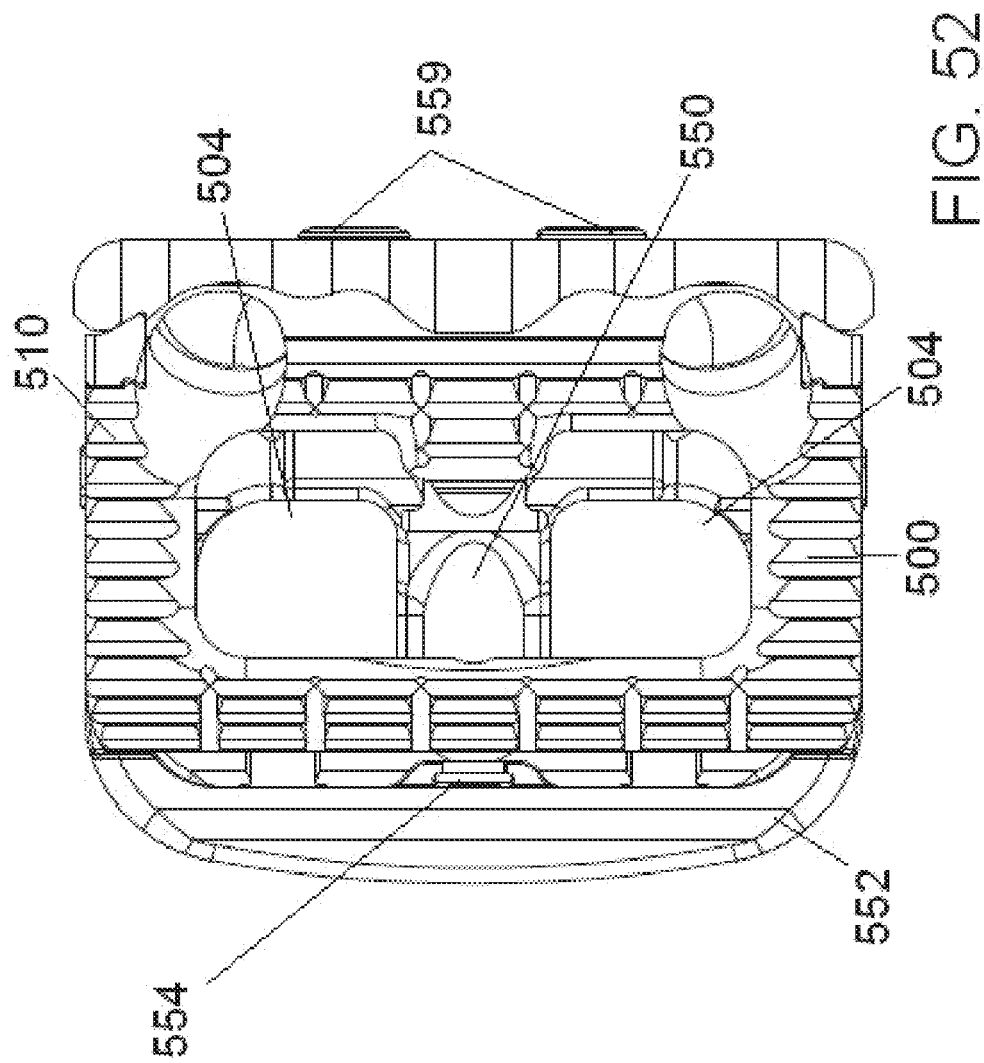
FIG. 52 is a top view of the implant of FIG. 51.

FIG. 52 is a top view of the implant of FIG. 51. From this view, one can see how the implant 500 advantageously includes a pair of graft windows 504 for receiving graft material therein. By providing a pair of graft windows 504, this advantageously increases the ability to promote bone fusion. Each of the graft windows 504 is offset from a central axis, thereby providing fusion in greater areas of the implant.

FIGS. 53A and 53B are different views of the implant of FIG. 51 in an unexpanded configuration. FIG. 53A is a front or anterior view of the implant 500, while FIG. 53B is a side view of the implant 500, in an unexpanded state.

As shown in FIG. 53A, one can see the first opening 513, second opening 515 and third opening 517 in the anterior of the implant 500. Each of the openings 513, 515, 517 corresponds with a socket 518 for receiving a bone screw therein—the first and second openings 513, 515 corresponding with a socket for receiving an upwardly facing bone screw and the third opening 517 corresponding with a socket for receiving a downwardly facing bone screw.

Figure 64:
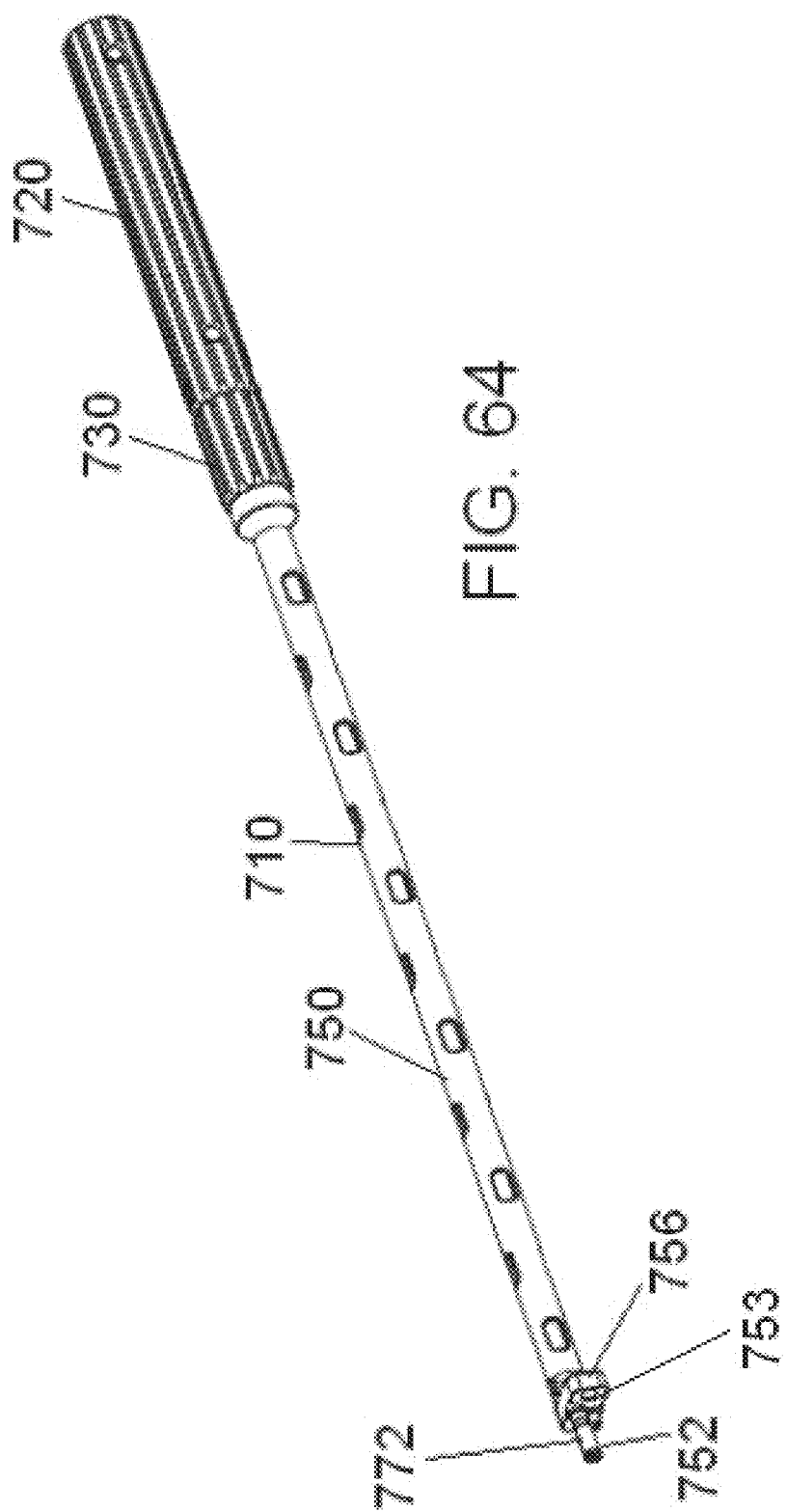
FIG. 64 is a top perspective view of an alternative insertion tool in accordance with some embodiments.

Within the first opening 513 and the second opening 515 are insertion tool openings 536 for receiving portions of an insertion tool, such as insertion tool 610 (shown in FIG. 55) or insertion tool 710 (shown in FIG. 64). In some embodiments, the insertion tool openings 536 are holes formed through the moveable actuator 550. In some embodiments, the insertion tool openings 536 can be multi-functional openings, whereby they can receive one or more tools, as well as provide an opening to provide graft material into the implant. Advantageously, the insertion tool can insert one or more extensions, prongs or tips into the insertion tool openings 536 to thereby grip the implant 500 to deliver it to a desired surgical site. Advantageously, the insertion tool openings 536 are each positioned between a middle axis and a lateral edge of the implant 500, thereby allowing a narrow insertion tool to be inserted into the implant 500. By providing a narrow insertion tool, this reduces the need to move tissue, such as the aorta or vena cava, which are at risk when contacted. These insertion tool openings 536 can be provided in addition to the lateral notches 519, thereby providing multiple means to grasp and insert the implant 500 into a surgical site.

To accommodate the openings 513, 515, 517 and/or insertion tool openings 536, the blocking fasteners 520 can include one or more cut-out portions 523 formed therein. For example, as shown in FIG. 53A, the lower blocking fastener 520 can have two cut-outs, thereby accommodating the first opening 513 and insertion tool opening 536 on one side, and the third opening 517 on another side. Likewise, the upper blocking fasteners 520 also have two cut-outs.

FIGS. 54A and 54B are different views of the implant of FIG. 51 in an expanded configuration. FIG. 54A is a front or anterior view of the implant 500, while FIG. 54B is a side view of the implant 500, in an expanded state.

As shown in FIG. 54A, the upper endplate 510 is configured to separate away from the lower endplate 512. As the endplates separate, the openings 513, 515, 517 split, such that partial openings 513*a*, 515*a*, 517*a* in the upper endplate move away from partial openings 513*b*, 515*b*, 517*b* in the lower endplate. In addition, the upper blocking fasteners 520 separate away from the lower blocking fastener 520.

Figure 55:
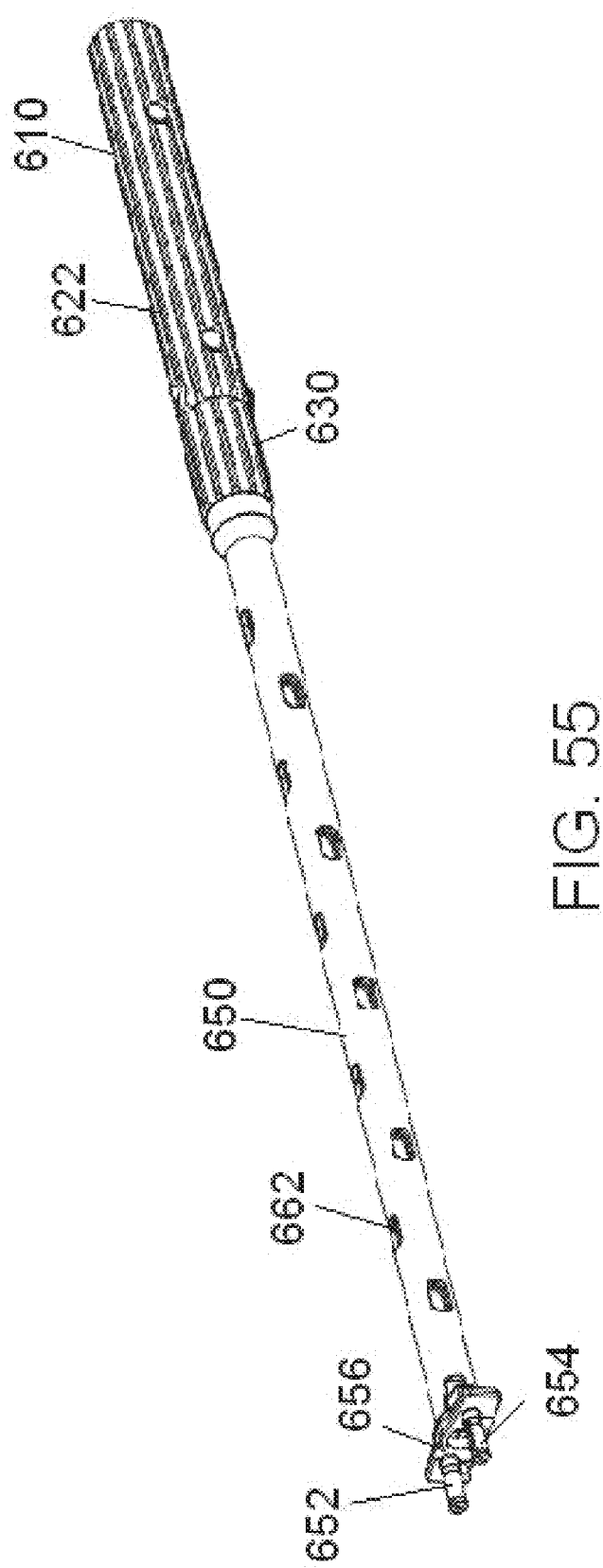
FIG. 55 is an insertion tool for an implant in accordance with some embodiments.
Figure 56:
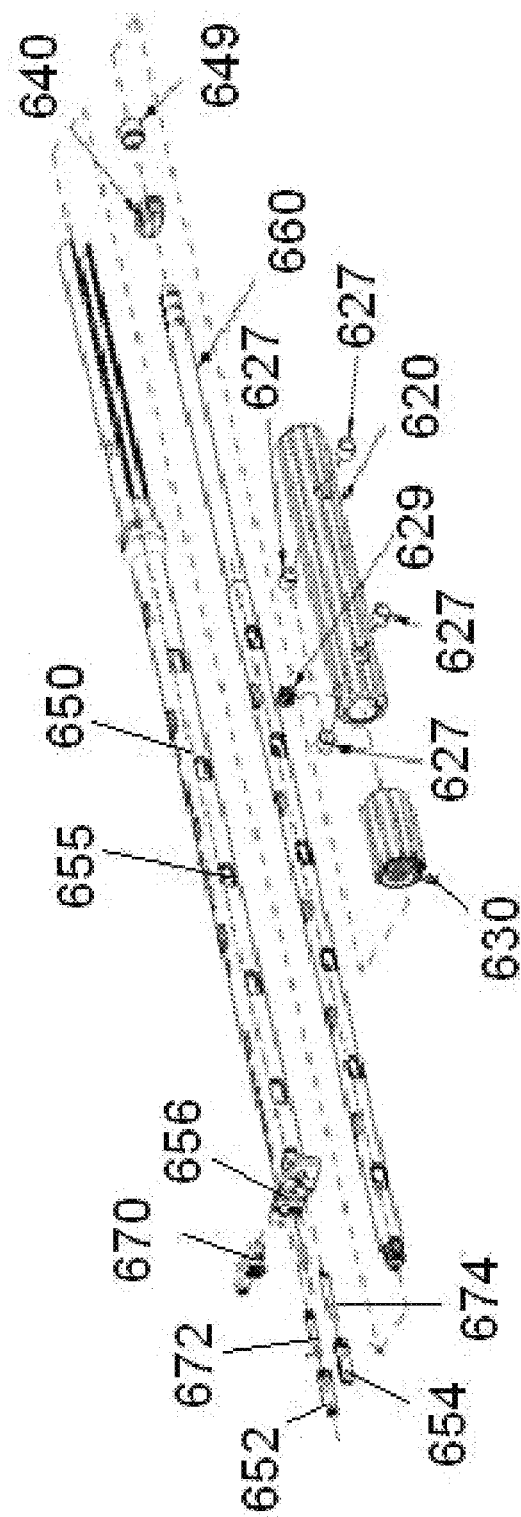
FIG. 56 is an exploded view of the insertion tool of FIG. 55.

FIG. 55 is an insertion tool for an implant in accordance with some embodiments, while FIG. 56 is an exploded view of the insertion tool. The insertion tool 610 is advantageously configured to be narrow, thereby reducing the need for soft tissue retraction. This is particularly useful in anterior lumbar interbody fusion surgeries, in which the aorta or vena cava can be an impediment during the surgery. By providing a narrow insertion tool 610, this advantageously reduces the risk of contacting these tissue and/or reduces the need for soft tissue retraction. In addition, in some embodiments, the insertion tool 610 is fully cannulated such that an additional tool or instrument can be inserted therethrough. For example, a driving instrument for actuating the actuator screw 554 of the implant 500 can be inserted through the insertion tool 610.

The insertion tool 610 comprises a handle 620, an actuator knob 630, an outer sleeve 650, and an inner plunger or retractor sleeve 660 (shown in FIG. 56). The outer sleeve 650 is configured to be attached to a pair of inserter tips 652, 654 that are capable of insertion into the insertion tool openings 662. The retractor sleeve 660 is configured to be attached to a pair of engagement pins 672, 674 that are capable of insertion into the pair of inserter tips 652, 654. When the engagement pins 672, 674 are inserted into the pair of inserter tips 652, 654 (as shown in FIG. 58), this causes the inserter tips 652, 654 to expand and be retained within the insertion tool openings 662 of the implant 600, thereby securing the insertion tool 610 to the implant 500 in a minimally invasive manner. With the insertion tool 610 secured to the implant 500, the implant 500 can then be delivered safely to a surgical site so that a surgical procedure can be performed.

The insertion tool 610 comprises an outer sleeve 650 for receiving the retractor sleeve 660 therein. The outer sleeve 650 comprises a shaft having one or more windows 662 formed therein. The windows 650 advantageously serve as openings for water to flush therethrough, thereby making the outer sleeve 650 easy to clean.

The shaft of the outer sleeve 650 comprises a proximal portion and a distal portion. At the proximal portion of the shaft, the outer sleeve 650 is connected to an actuator knob 630 and a handle 620. The handle 620 can be connected to the retractor sleeve 660 via pins 627 and set screw 629. Rotation of the actuator knob 630 results in translation of the retractor sleeve 660 within the outer sleeve 650. As the retractor sleeve 660 translates, this causes the engagement pins 672, 674 to extend further distally into the inserter tips 652, 654, thereby causing the inserter tips 652, 654 to expand. This converts the insertion tool 610 from a retracted configuration to an engaged configuration, whereby the implant 500 is securely held to the insertion tool 610.

At the distal portion of the shaft, the outer sleeve 650 is connected to a plate portion 656 from which a pair of inserter tips 652, 654 extend therefrom. Advantageously, the plate portion 656 helps to position the insertion tool 610 steadily against an implant 500. The pair of inserter tips 652, 654 are configured to be inserted into the insertion tool openings 536 formed in the implant 500. As shown in FIG. 57, each of the inserter tips 652, 654 includes at least one slit formed therethrough. The slit advantageously allows for expansion of the inserter tips 652, 654 when engagement pins 672, 674 are received therein. When the pair of inserter tips 652 are in an unexpanded configuration, they are capable of being received within the insertion tool openings 536 formed in the implant 500. Once the inserter tips 652 are placed within the insertion tool openings 536, the inserter tips 652 can be expanded by inserting the engagement pins 672, 674 therethrough, thereby causing the insertion tool 610 to be secured to the implant 500. The implant can then be delivered to a surgical site for a surgical procedure.

As shown in FIG. 56, an inner or retractor sleeve 660 is received within the shaft of the outer sleeve 650. The retractor sleeve 660 comprises a shaft having a proximal portion and a distal portion. The proximal portion of the shaft is attached to a threaded block 640. The threaded block 640 is designed to provide outer threads that engage inner threads of the actuator knob 630. This advantageously provides an assembly whereby the outer sleeve 650 is attached to the actuator knob 630, and the actuator knob 630 is attached to the retractor sleeve 660 via the threaded block 640. Rotation of the actuator knob 630 thus causes linear translation of the retractor sleeve 660 within the outer sleeve 650. A retaining sleeve 649 can be positioned proximal to the threaded block 640 to retain the threaded block 640 on the retractor sleeve 660.

In some embodiments the distal portion of the retractor sleeve 660 is attached to an actuator tip 670 from which a pair of engagement pins 672, 674 extend. In some embodiments, the engagement pins 672, 674 can have a bullet-shaped portion that is capable of extending into the inserter tips 652, 654. By providing a bullet-shaped portion, this allows the engagement pins 672, 674 to be partially inserted into the inserter tips 652, 654 without causing expansion of the inserter tips 652, 654. In some embodiments, only when the engagement pins 672, 674 are inserted far enough into the inserter tips 652, 654 (e.g., such as when the apex of the bullet-shaped portion contacts the inner walls of the inserter tips), will expansion of the inserter tips 652, 654 occur, thereby securing the insertion tool 610 to an implant 500.

FIG. 57 is a close-up view of the insertion tool of FIG. 55 with an implant in a retracted configuration or position. In the retracted position, the engagement pins 672, 674 of the inner retractor sleeve 660 have yet to be inserted distally enough into the inserter tips 652, 654 to cause expansion of the inserter tips 652, 654. With the inserter tips 652, 654 unexpanded, the insertion tool 610 is capable of insertion into the insertion tool openings 538 (shown in FIG. 53A) in the implant 500 with ease. Once inserted therein, the insertion tool 610 can be converted into an extended configuration or position, whereby the inserter tips 652, 654 expand and securely engage the implant 500.

FIG. 58 is a close-up view of the insertion tool of FIG. 55 with an implant in an engaged position. To convert the insertion tool from the retracted position to the engaged position, the actuator knob 630 (shown in FIG. 55) is rotated. In the engaged position, the engagement pins 672, 674 of the inner retractor sleeve 660 have been inserted further distally into the inserter tips 652, 654, thereby causing expansion of the inserter tips 652, 654. With the inserter tips 652, 654 expanded, the insertion tool 610 is secured to the implant 500, and thus capable of delivering the implant to a surgical site.

FIG. 59 is top view of the insertion tool of FIG. 55 with an implant in an engaged position. From this view, one can see how the plate portion 656 of the outer sleeve 650 is positioned adjacent to and abuts the anterior surface of the implant 500. From this view, one can also see where the inserter tips 652, 654 penetrate the implant 500. As shown in FIG. 59, the inserter tips 652, 654 can extend through an anterior portion of the implant and extend as far as the graft openings 504.

FIG. 60 is a top perspective view of the insertion tool of FIG. 55 attached to an implant, while FIG. 61 is a top perspective view of the insertion tool of FIG. 55 detached from an implant. From these views, one can see how the inserter tips 652, 654 of the insertion tool 610 are insertable into the implant 500.

FIG. 62 is a close-up cross-sectional view of the insertion tool of FIG. 55 with an implant in a retracted position, while FIG. 63 shows a close-up view in an engaged position. From this view, one can see how even in the retracted position, at least a portion of the engagement pins 672, 674 can reside in the inserter tips 652, 654, thereby causing minimal, if any, expansion of the inserter tips 652, 654. As shown in the figure, the distal portions of the engagement pins 672, 674 are bullet-shaped. Also, from this view, one can see how the retractor sleeve 660 is attached to the actuator tip 670 having engagement pins 672, 674 extending therefrom via a threaded interface 673.

Figure 65:
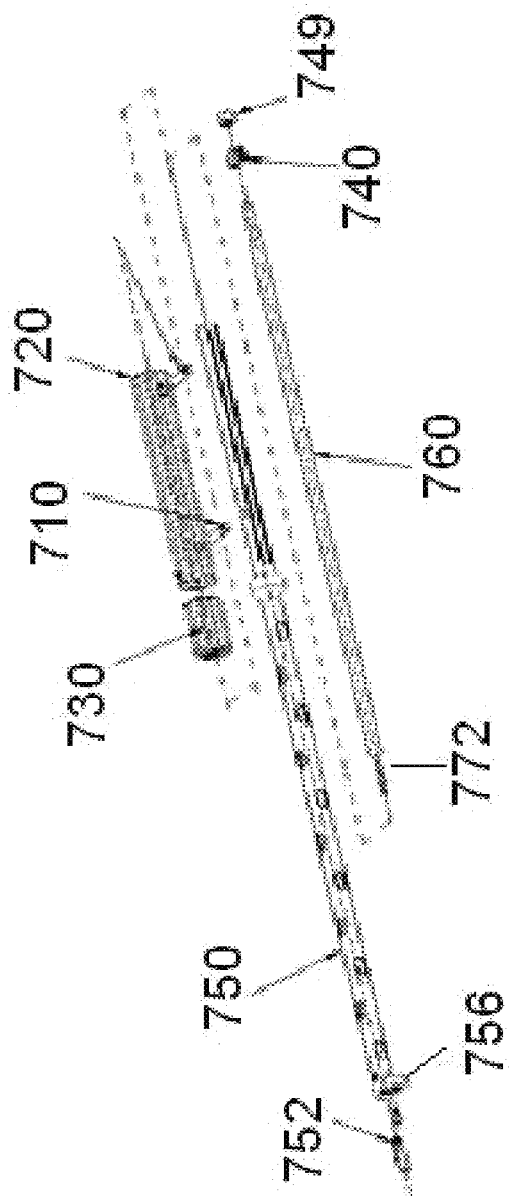
FIG. 65 is an exploded view of the insertion tool of FIG. 64.

FIG. 64 is a top perspective view of an alternative insertion tool in accordance with some embodiments, while FIG. 65 shows an exploded view of the insertion tool. The insertion tool 710 has similar features to the prior insertion tool 610, but includes only a single, offset inserter tip 752 for inserting into an implant 500. In some embodiments, the insertion tool 710 can be of even narrower profile than the insertion tool 610, thereby reducing the need for soft tissue retraction. In the present embodiment, the insertion tool 710 includes an offset channel 753 for receiving a driver or other instruments therein. In other embodiments, the insertion tool 710 is fully cannulated so as to allow one or more additional tools or instruments to be inserted therein. For example, in some embodiments, a driving tool can be inserted through the cannulated insertion tool 710 to actuate the actuator screw 554 of the implant 500.

Insertion tool 710 comprises an outer sleeve 750, an inner plunger or retractor sleeve 760, an actuator knob 730 and a handle 720. The insertion tool 710 is assembled in a similar manner to the insertion tool 610. In some embodiments, the outer sleeve 750 comprises a shaft having a proximal portion and a distal portion. On the proximal portion, the actuator knob 730 is attached to the outer sleeve 750, which is in turn connected to the handle 720. On the distal portion, a distal plate 756 is attached, from which only a single offset inserter tip 752 is provided. The inserter tip 752 includes at least one slit that allows it to expand.

Figure 68:
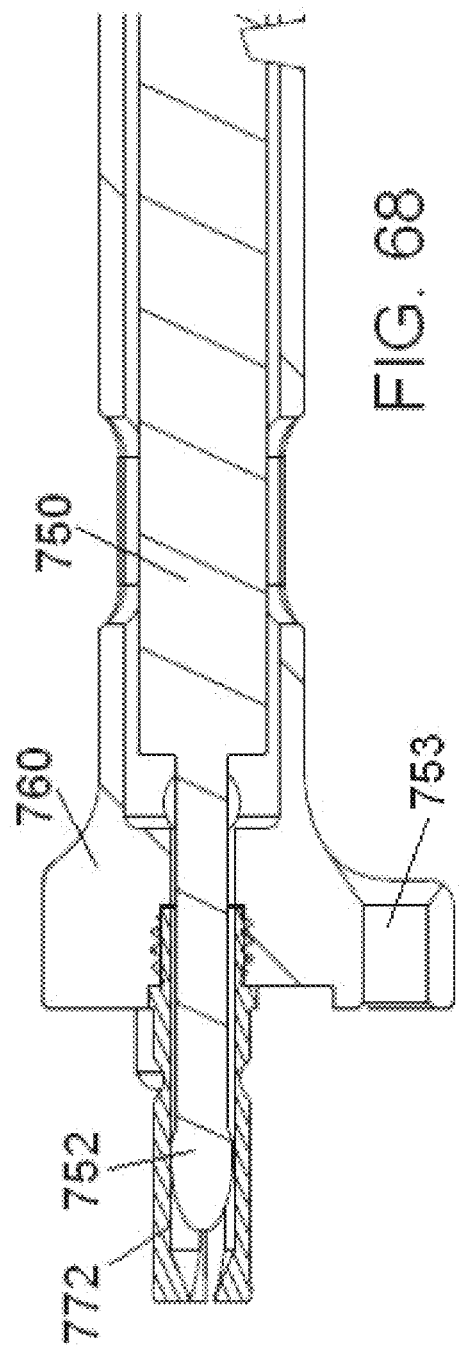
FIG. 68 is a close-up cross-sectional view of the insertion tool of FIG. 64 in a retracted position.
Figure 69:
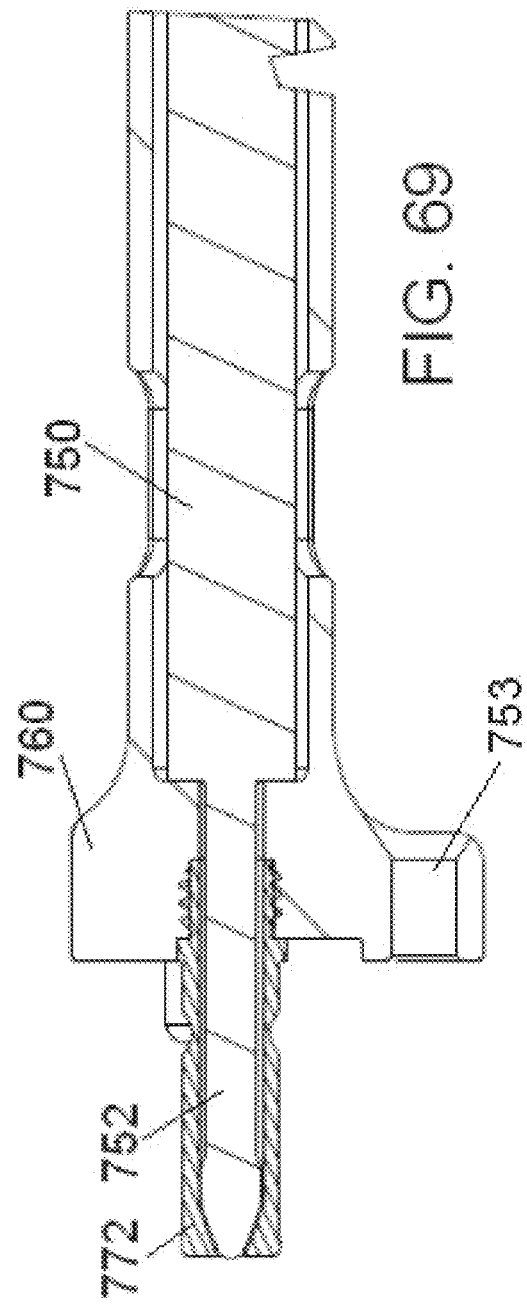
FIG. 69 is a close-up cross-sectional view of the insertion tool of FIG. 64 in an engaged position.
Figure 70:
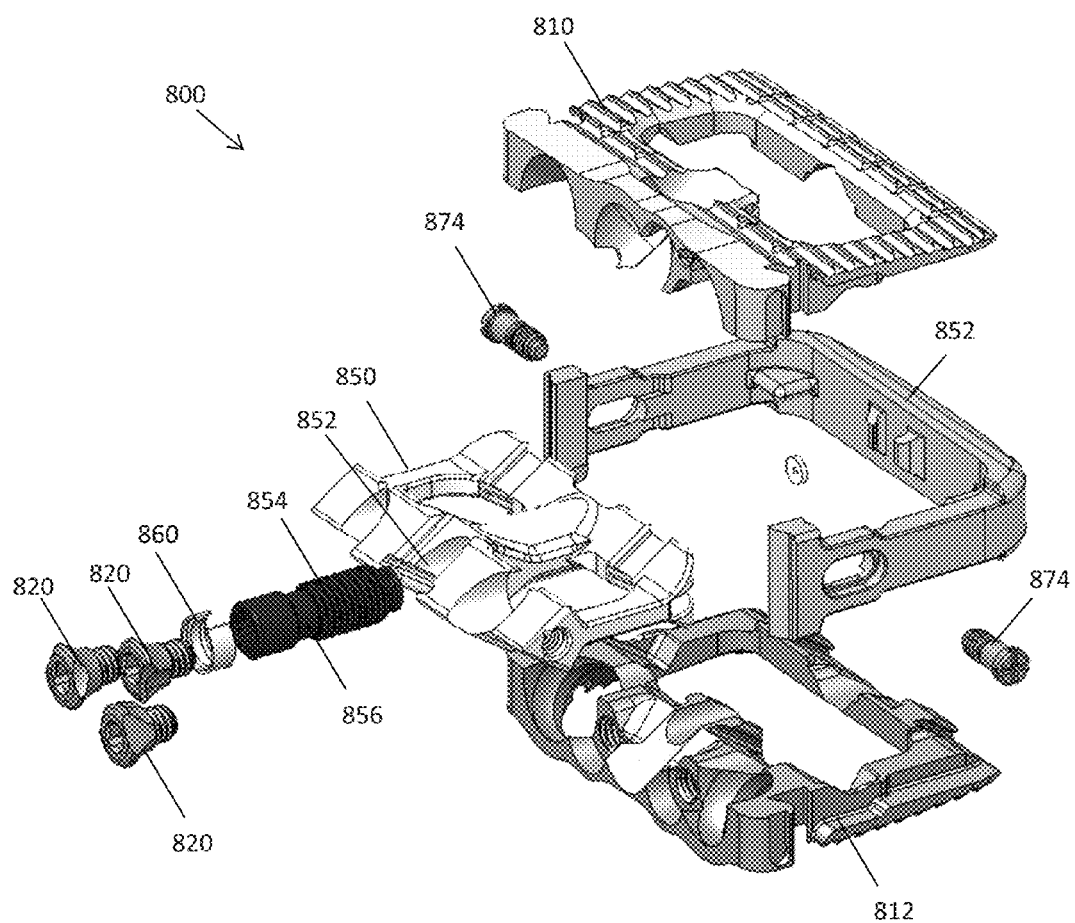
FIG. 70 is an exploded view of an alternative implant in accordance with some embodiments.
Figure 71:
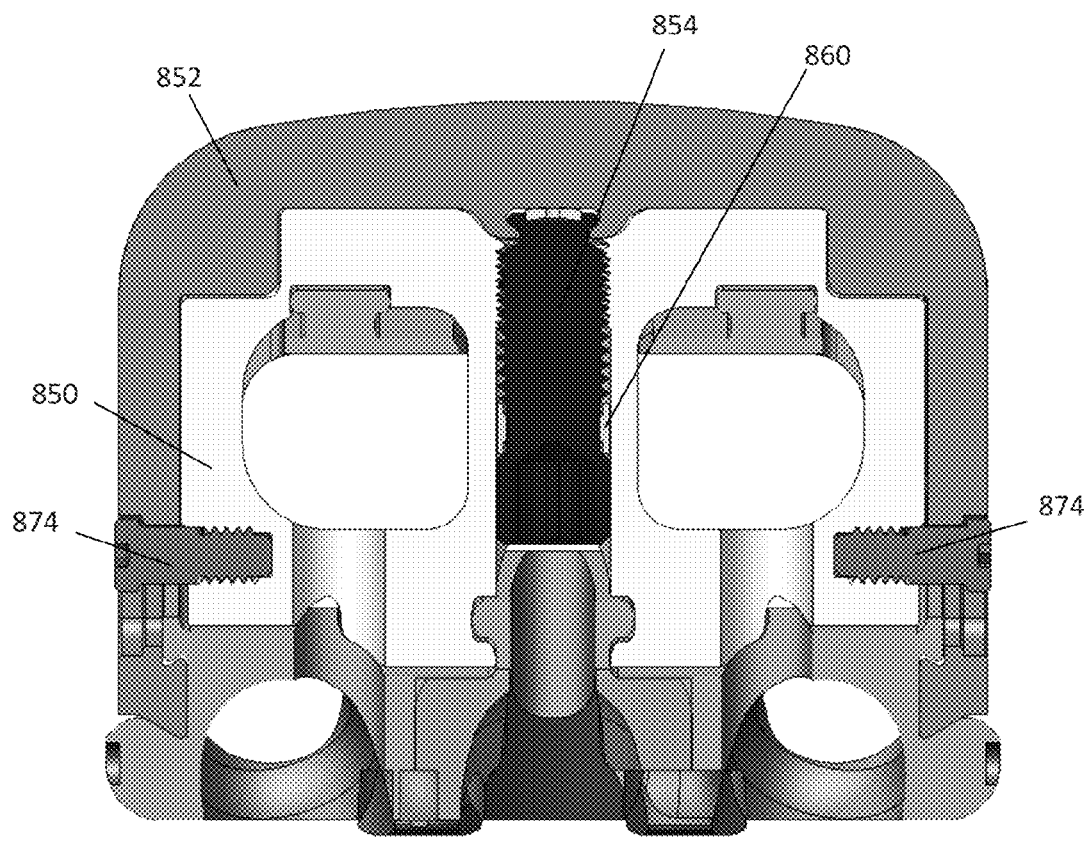
FIG. 71 is a top partial cross-sectional view of the implant of FIG. 70.
Figure 72:
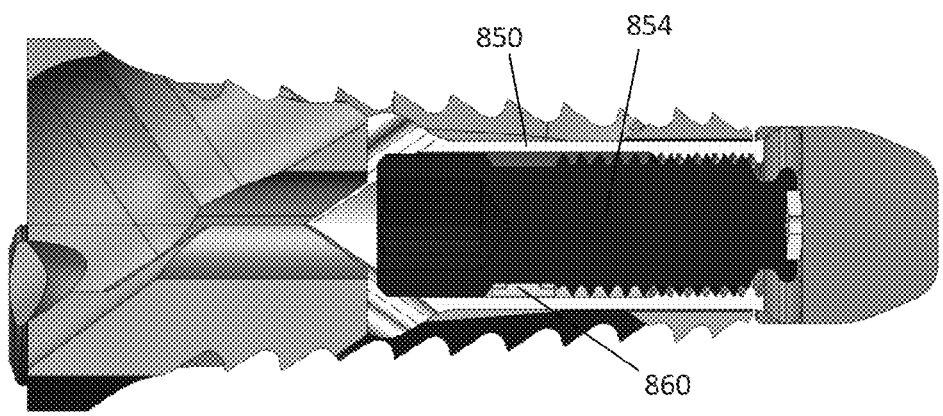
FIG. 72 is a side partial cross-sectional view of the implant of FIG. 70.

The outer sleeve 750 is capable of receiving the retractor sleeve 760 therein. The retractor sleeve 760 comprises a shaft having a proximal portion and a distal portion. On the proximal portion, a threaded block 740 is attached to the retractor sleeve 760. The threaded block 760 includes outer threads that engage with inner threads of the actuator knob 730, which is in turn connected to the outer sleeve 750. A retaining sleeve 749 can be positioned proximal to the threaded block 740 to retain the threaded block 740 on the retractor sleeve 760. On the distal portion, an offset engagement pin 772 extends from the shaft (as shown in FIGS. 68 and 69). The engagement pin 772 is capable of extending through the inserter tip 752, thereby causing expansion of the inserter tip 752 to secure the insertion tool 710 to the implant 500.

FIG. 66 is a close-up view of the insertion tool of FIG. 64 in a retracted position, while FIG. 67 is a close-up view of the insertion tool in an engaged position. In the retracted position, the engagement pin 772 is received within the inserter tip 752, but only to the point where the inserter tip 752 has negligible, if any, expansion. In the engaged position, the engagement pin 772 is inserted further distally into the inserter tip 752, thereby causing expansion of the inserter tip 752. In the retracted position, the insertion tool 710 is capable of inserting into one of the insertion tool openings 536 of the implant 500. Once the insertion tool 710 is inserted through an opening 536, the insertion tool 710 can be converted into the engaged position, whereby the inserter tip 752 is expanded to secure the insertion tool 710 to the implant 500.

FIG. 68 is a close-up cross-sectional view of the insertion tool of FIG. 64 in a retracted position, while FIG. 69 is a close-up cross-sectional view of the insertion tool in an engaged position. From these views, one can see how the sole engagement pin 772 can extend from the distal end of the retractor sleeve 760 body. In both the retracted position and the engaged position, the insertion tool 710, including all of its components, are offset from a central longitudinal axis that extends through the implant, thereby advantageously helping to further avoid soft tissue contact.

Turning now to FIGS. 70-74, an implant 800, similar to implant 500, and its subcomponents are shown. Implant 800 shares similar features as previous embodiments described herein, including an upper endplate 810 and an opposed lower endplate 812, and a frame 852 positioned between the upper endplate 810 and the lower endplate 812. A moveable actuator 850 with one or more ramps is positioned within the body of the frame 852. The actuator 850 is operably connected to the frame 852 with one or more support screws 874. A partially threaded actuator screw 854 extends through an opening 852 in the actuator 850. By rotating the actuator screw 854 in a first direction, the actuator 850 linear translates, thereby causing the upper endplate 810 and the lower endplate 812 to expand and separate away from one another. By rotating the actuator screw 854 in a second direction opposite to the first direction, causes the actuator 850 to linear translate in the opposite direction, thereby causing the upper endplate 810 and the lower endplate 812 to contract and move toward one another. One or more fixation or bone members (not shown) are positionable through each of the upper endplate 810 and the lower endplate 812, to secure the implant 800 to adjacent vertebrae. One or more blocking elements 820 can be provided to reduce the risk of inadvertent back out of the bone members.

In this embodiment, the actuator screw 854 also includes a friction sleeve 860. The friction sleeve 860 improves the consistency of fit and function of the assembled implant 800 when it is being expanded or contracted. The friction sleeve 860 also prevents unwanted rotation of the actuator screw 854, for example, when the actuator screw 854 is not being purposefully rotated by a user (e.g., under compression force between two adjacent vertebrae). Thus, the friction sleeve 860 may act as a safety mechanism to prevent undesired contraction or expansion of the implant 800.

Figure 73:
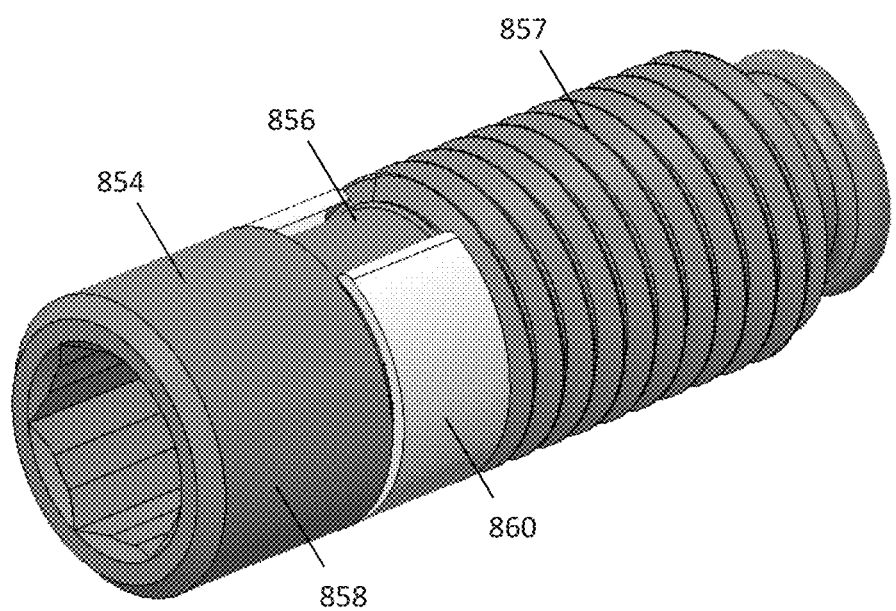
FIG. 73 is a perspective view of the actuator screw used in the implant of FIG. 70.
Figure 74:
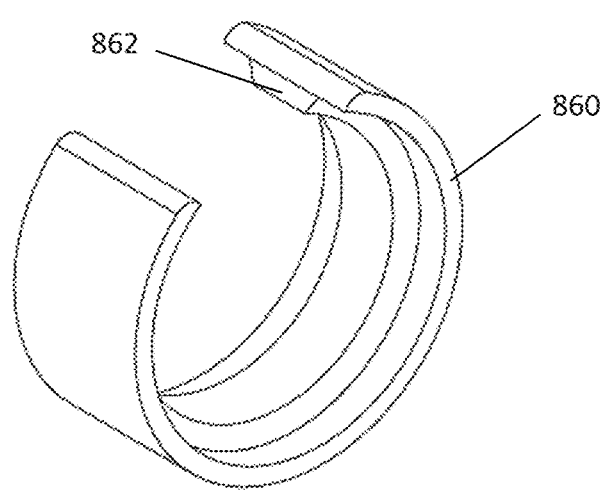
FIG. 74 is a perspective view of a friction sleeve used with the actuator screw of FIG. 73.

The friction sleeve 860 fits over a groove 856 on the actuator screw 854. For example, the friction sleeve 860 may attach to the actuator screw 854 with a snap-fit type engagement. The groove 856 may extend around a portion of or around the entire circumference of the actuator screw 854. The friction sleeve 860 may be in the shape of a ring or a partial ring. As best seen in FIGS. 73 and 74, the friction sleeve 860 may have a substantially c-shaped body configured to engage with the actuator screw 854. The c-shaped body may include a gap between two ends of the friction sleeve 860 to allow the friction sleeve 860 to be placed around the groove 856 and removed from the actuator screw 854 if desired.

The actuator screw 854 may extend from a first end having a recess configured to receive a driving instrument, for example, the hex head of a screw driver to a second end configured to be received in the opening 852 in the actuator 850. The actuator screw 854 may have a threaded portion 857 and a non-threaded portion 858. For example, the non-threaded portion 858 may be positioned proximate to the first end with the driver recess. The groove 856 may be positioned between the threaded portion 857 and the non-threaded portion 858. The groove 856 may have a depth such that an outer surface of the friction sleeve 860 is substantially flush with the non-threaded portion 858 of the actuator screw 854. The friction sleeve 860 may also include one or more protrusions 862, for example, extending along an inner surface of the friction sleeve 860. The protrusion 862 may be sized and dimensioned to be received within a corresponding recess in the groove 856 of the actuator screw 854. The protrusion 862 may have angled sidewalls, which engage corresponding sidewalls of the groove 856 in the actuator screw 854. The friction sleeve 860 may be comprised of material with a higher coefficient of friction than the material of the actuator screw 854 and/or the actuator 850. For example, the friction sleeve 860 may be comprised of a biocompatible plastic, such as polyether ether ketone (PEEK) whereas the actuator screw 854 and actuator 850 may be comprised of a biocompatible metal, such as titanium or a titanium alloy.

The actuator screw 854 together with the friction sleeve 860 fit inside the through-hole or opening 852 in the actuator 850. The opening 852 may extend through the entire length of the actuator 850 or a portion thereof. The friction sleeve 860 is dimensioned to interfere with the outer diameter of the actuator screw 854 and the inner diameter of the through-hole or opening 852 in the actuator 850. With this interference, friction is created between the actuator screw 854 and the actuator 850 in order to prevent unwanted rotation of the actuator screw 854. In addition, the interference and friction improves the consistency of the feel of the actuator screw 854 in the assembled implant 800.

In some embodiments, the implants and associated instruments described above can be used with other surgical systems and implants. For example, any of the implants can be used with and benefit from surgical screws, rods, and plates. In addition, in some embodiments, the implants can be inserted on one level, and different implants (e.g., fusion or prosthetic) can be inserted in another spinal level.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An intervertebral implant comprising:
   an upper endplate;
   a lower endplate;
   a frame;
   a moveable actuator at least partially received in the frame and positioned between the upper endplate and the lower endplate;
   an actuator screw having a groove, the actuator screw extends through the moveable actuator, wherein rotation of the actuator screw in a first direction causes the moveable actuator to translate, thereby causing the implant to change from an unexpanded configuration to an expanded configuration; and
   a friction sleeve positioned in the groove and coupled to the actuator screw which prevents unwanted rotation of the actuator screw, wherein the friction sleeve includes a protrusion extending along an inner surface of the friction sleeve, and the protrusion is sized and dimensioned to be received within a corresponding recess in the groove of the actuator screw.

2. The implant of claim 1, wherein the groove has angled sidewalls corresponding to angled side walls on the protrusion.

3. The implant of claim 1, wherein the groove extends around the entire circumference of the actuator screw.

4. The implant of claim 1, wherein the friction sleeve is attached to the actuator screw with a snap-fit type engagement.

5. The implant of claim 1, wherein the friction sleeve is in the shape of a partial ring.

6. The implant of claim 1, wherein the actuator screw has a threaded portion and a non-threaded portion.

7. The implant of claim 6, wherein the friction sleeve fits over the groove on the actuator screw, and wherein the groove is positioned between the threaded portion and the non-threaded portion.

8. The implant of claim 7, wherein the groove has a depth such that an outer surface of the friction sleeve is substantially flush with the non-threaded portion of the actuator screw.

9. The implant of claim 1, wherein the friction sleeve has a higher coefficient of friction than the actuator screw and the actuator.

10. The implant of claim 1, wherein the friction sleeve is dimensioned to interfere with an outer diameter of the actuator screw and an inner diameter of the actuator.

11. An intervertebral implant comprising:
    an upper endplate;
    a lower endplate;
    a frame;
    a moveable actuator at least partially received in the frame and positioned between the upper endplate and the lower endplate;
    an actuator screw that extends through the moveable actuator, wherein rotation of the actuator screw in a first direction causes the moveable actuator to translate, thereby causing the implant to change from an unexpanded configuration to an expanded configuration; and
    a friction sleeve received in a groove on the actuator screw, wherein the friction sleeve has a higher coefficient of friction than the actuator screw and the actuator, wherein the friction sleeve includes a protrusion extending along an inner surface of the friction sleeve, and the protrusion is sized and dimensioned to be received within a corresponding recess in the groove of the actuator screw.

12. The implant of claim 11, wherein the groove extends around the entire circumference of the actuator screw.

13. The implant of claim 11, wherein the friction sleeve is attached to the actuator screw with a snap-fit type engagement.

14. The implant of claim 11, wherein the friction sleeve is in the shape of a partial ring.

15. The implant of claim 11, wherein the actuator screw has a threaded portion and a non-threaded portion.

16. The implant of claim 15, wherein the groove is positioned between the threaded portion and the non-threaded portion.

17. The implant of claim 16, wherein the groove has a depth such that an outer surface of the friction sleeve is substantially flush with the non-threaded portion of the actuator screw.

18. The implant of claim 11, wherein the friction sleeve includes one or more protrusions extending along an inner surface of the friction sleeve.

19. The implant of claim 11, wherein the friction sleeve is dimensioned to interfere with an outer diameter of the actuator screw and an inner diameter of the actuator.

* * * * *